(12) United States Patent
Carton et al.

(10) Patent No.: US 8,663,980 B2
(45) Date of Patent: Mar. 4, 2014

(54) VECTORS, HOST CELLS, AND METHODS OF PRODUCTION AND USES

(75) Inventors: Jill Carton, Radnor, PA (US); Jin Lu, Radnor, PA (US); Bernard J. Scallon, Radnor, PA (US); Linda Snyder, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 755 days.

(21) Appl. No.: 12/738,453

(22) PCT Filed: Oct. 24, 2008

(86) PCT No.: PCT/US2008/081090
§ 371 (c)(1),
(2), (4) Date: Sep. 16, 2010

(87) PCT Pub. No.: WO2009/055656
PCT Pub. Date: Apr. 30, 2009

(65) Prior Publication Data
US 2011/0008321 A1    Jan. 13, 2011

Related U.S. Application Data

(60) Provisional application No. 60/982,814, filed on Oct. 26, 2007.

(51) Int. Cl.
C12N 15/79 (2006.01)
C12P 21/08 (2006.01)

(52) U.S. Cl.
USPC .................................. 435/320.1; 435/70.1

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,873,316 A | 10/1989 | Meade et al. |
| 5,225,539 A | 7/1993 | Winter |
| 5,304,489 A | 4/1994 | Rosen |
| 5,530,101 A | 6/1996 | Queen et al. |
| 5,545,806 A | 8/1996 | Lonberg et al. |
| 5,565,362 A | 10/1996 | Rosen |
| 5,569,825 A | 10/1996 | Lonberg et al. |
| 5,585,089 A | 12/1996 | Queen et al. |
| 5,625,126 A | 4/1997 | Lonberg et al. |
| 5,625,825 A | 4/1997 | Rostoker et al. |
| 5,633,425 A | 5/1997 | Lonberg et al. |
| 5,661,016 A | 8/1997 | Lonberg et al. |
| 5,693,762 A | 12/1997 | Queen et al. |
| 5,714,352 A | 2/1998 | Jakobovits |
| 5,723,323 A | 3/1998 | Kauffman et al. |
| 5,763,192 A | 6/1998 | Kauffman et al. |
| 5,766,886 A | 6/1998 | Studnicka et al. |
| 5,770,428 A | 6/1998 | Boris-Lawrie |
| 5,789,650 A | 8/1998 | Lonberg et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,827,690 A | 10/1998 | Meade et al. |
| 5,849,992 A | 12/1998 | Meade et al. |
| 5,976,862 A | 11/1999 | Kauffman et al. |
| 5,994,616 A | 11/1999 | Rosen |
| 6,180,370 B1 | 1/2001 | Queen et al. |
| 6,204,023 B1 | 3/2001 | Robinson et al. |
| 2002/0055173 A1 | 5/2002 | Parks et al. |
| 2005/0196755 A1* | 9/2005 | Zauderer et al. ................. 435/6 |
| 2007/0107075 A1 | 5/2007 | Klein et al. |

FOREIGN PATENT DOCUMENTS

| | | |
|---|---|---|
| EP | 0229246 B1 | 7/1987 |
| EP | 0264166 B1 | 4/1988 |
| WO | WO 90/05370 A1 | 5/1990 |
| WO | WO 90/11354 A1 | 10/1990 |
| WO | WO 90/14424 A1 | 11/1990 |
| WO | WO 90/14430 A1 | 11/1990 |
| WO | WO 90/14443 A1 | 11/1990 |
| WO | WO 91/01140 A1 | 2/1991 |
| WO | WO 92/00968 A1 | 1/1992 |
| WO | WO 92/01047 A1 | 1/1992 |
| WO | WO 92/03461 A1 | 3/1992 |
| WO | WO 92/11272 A1 | 7/1992 |
| WO | WO 93/04169 A1 | 3/1993 |
| WO | WO 93/06213 A1 | 4/1993 |
| WO | WO 94/18219 A1 | 8/1994 |
| WO | WO 97/07668 A1 | 3/1997 |
| WO | WO 97/07669 A1 | 3/1997 |
| WO | WO 97/20032 A1 | 6/1997 |
| WO | WO 98/50433 A2 | 11/1998 |
| WO | WO 99/06834 A2 | 2/1999 |
| WO | WO2006/071804 A2 | 7/2006 |
| WO | WO2007/045465 A1 | 4/2007 |

OTHER PUBLICATIONS

PCT International Search Report dated May 20, 2009.
Trill, et al., "Production of Monoclonal antibodies in COS and CHO cells," Current Opinion in Biotechnology, 6: 553-560 (1995).
Gillies, et al., "A Tissue-specific Transcription Enhancer Element is Located in the Major Intron of a Rearranged Immunoglobulin Heavy Chain Gene," Cell, 33: 717-728 (1983).
Norderhaug, et al., "Versatile vectors for transient and stable expression of recombinant antibody molecules in mammalian cells," Journal of Immunological Methods, 204: 77-87 (1997).
EP Communication/Office Action dated Jan. 31, 2013.

(Continued)

*Primary Examiner* — Michael Burkhart
(74) *Attorney, Agent, or Firm* — Eric Dichter

(57) ABSTRACT

Antibody expression vectors and plasmids can incorporate various antibody gene portions for transcription of the antibody DNA and expression of the antibody in an appropriate host cell. The expression vectors and plasmids have restriction enzyme sites that facilitate ligation of antibody-encoding DNA into the vectors. The vectors incorporate enhancer and promoter sequences that can be varied to interact with transcription factors in the host cell and thereby control transcription of the antibody-encoding DNA. A kit can incorporate these vectors and plasmids.

11 Claims, 4 Drawing Sheets

(56) References Cited

OTHER PUBLICATIONS

Amann, et al., "Tightly regulated *tac* promoter vectors useful for the expression of unfused and fused proteins in *Escherichia coli*," Gene, 69: 301-315 (1988).
Baldari, et al., "A novel leader peptide which allows efficient secretion of a fragment of human interleukin 1β in *Saccharomyces cerevisiae*," The EMBO Journal, 6(1): 229-234 (1987).
Banerjii, et al., "A Lymphocyte-Specific Cellular Enhancer is Located Downstream of the Joining Region in Immunoglobulin Heavy Chain Genes," Cell, 33: 729-740 (1983).
Allan Bradley, "Modifying the mammalian genome by gene targeting," Current Opinion in Biotechnology, 2: 823-829 (1991).
Allan Bradley, "Production and analysis of chimaeric mice," Teratocarcinomas and Embryonic Stem Cells: a Practical Approach, Chapter 5, 113-152 Robertson ed. (1987).
Byrne, et al., "Multiplex gene regulation: A two-tiered approach to transgene regulation in transgenic mice," Proceedings of the National Academy of Science USA, 86: 5473-5477 (1989).
Calame, et al., "Transcriptional Controlling Elements in the Immunoglobulin and T Cell Receptor Loci," Advances in Immunology, 43: 235-275 (1988).
Camper, et al., "Postnatal repression of the alpha-fetoprotein gene is enhancer independent," Genes Development, 3: 537-546 (1989).
Carter, et al., "Humanization of anti-p185$^{HER2}$ antibody for human cancer therapy," Proceedings of the National Academy of Science USA, 89: 4285-4289 (1992).
Chothia, et al., "Canonical Structures for the Hypervariable Regions of Immunoglobulins," Journal of Molecular Biology, 196: 901-917 (1987).
Edlund, et al., "Cell-Specific Expression of the Rat Insulin Gene: Evidence for Role of Two Distinct 5' Flanking Elements," Science, 230: 912-916 (1985).
Evan, et al., "Isolation of Monoclonal Antibodies Specific for Human c-myc Proto-Oncogene Product," Molecular and Cellular Biology, 5(12): 3610-3616 (1985).
Field, et al., "Purification of a *RAS*-Responsive Adenylyl Cyclase Complex from *Saccharomyces cerevisiae* by Use of an Epitope Addition Method," Molecular and Cellular Biology, 8(5): 2159-2165 (1988).
Fishwild, et al., "High-avidity human IgGκ monoclonal antibodies from a novel strain of minilocus transgenic mice," Nature Biotechnology, 14: 845-851 (1996).
Goessling, et al., "MATCH™—a tool for searching transcription factor binding sites in DNA sequences. Application for the analysis of human chromosomes," German Conference on Bioinformatics, Oct. 7-10, 2001. Abstract.
Susan Gottesman, "Minimizing Proteolysis in *Escherichia coli*: Genetic solutions," Gene Expression Technology: Methods in Enzymology 185, Academic Press, pp. 60-89 (1990).
Green, et al., "Antigen-specific human monoclonal antibodies from mice engineered with human Ig heavy and light chain YACs," Nature Genetics, 7: 13-21 (1994).
Henderson, et al., "Transcriptional Regulation During B Cell Development," Annual Review of Immunology, 16: 163-200 (1998).
Hopp, et al., "A Short Polypeptide Marker Sequence Useful for Recombinant Protein Identification and Purification," Bio/Technology, 6: 1204-1210 (1988).
Jones, et al., "Replacing the complementarity—determining regions in a human antibody with those from a mouse," Nature, 321: 522-326 (1986).
Kaufman, et al, "Translational efficiency of polycistronic mRNAs and their utilization to express heterologous genes in mammalian cells," The BMBO Journal, 6(1): 187-193 (1987).
Kessel, et al., "Murine Developmental Control Genes," Science, 249: 374-379 (1990).
Kurjan, et al., "Structure of a Yeast Pheromone Gene (*MFα*): A Putative α-Factor Precursor Contains Four Tandem Copies of Mature α-Factor," Cell, 30: 933-943 (1982).

Lasko, et al., "Targeted oncogene activation by site-specific recombination in transgenic mice," Proceedings of the National Academy of Science USA, 89: 6232-6236 (1992).
Li, et al., "Targeted Mutation of the DNA Methyltransferase Gene Results in Embryonic Lethality," Cell, 69: 915-926 (1992).
Lonberg, et al., "Human Antibodies from Transgenic Mice," Internal Review of Immunology, 13: 65-93 (1995).
Lonberg, et al., "Antigen-specific human antibodies from mice comprising four distinct genetic modifications," Nature, 368: 856-859 (1994).
Looney, et al., "High-level expression and characterization of a mouse-human Chimeric CD4 antibody with therapeutic potential," Human Antibodies Hybridomas, 3: 191-200 (1992).
Luckow, et al., "High Level Expression of Nonfused Foreign Genes with Autographa californica Nuclear Polyhedrosis Virus Expression Vectors," Virology, 170: 31-39 (1989).
Lutz, et al., "Quantitative determination that one of two potential RNA-binding domains of the A protein component of the U1 small nuclear ribonucleoprotein complex bind with high affinity to stem-loop II of U1 RNA," Proceedings of the National Academy of Science USA, 87: 6393-6397 (1990).
Martin, et al., "GAP Domains Responsible for Ras p21-Dependent Inhibition of Muscarinic Atrial K$^+$Channel Currents," Science, 255: 192-194 (1992).
Matys, et al., "TRANSFAC®: transcriptional regulation, from patterns to profiles," Nucleic Acids Research, 31(1): 374-378 (2003).
Mendez, et al., "Functional transplant of megabase human immunoglobulin loci recapitulates human antibody response in mice," Nature Genetics, 15: 146-156 (1997).
O'Gorman, et al., "Recombinase-Mediated Gene Activation and Site-Specific Integration in Mammalian Cells," Science, 251: 1351-1355 (1991).
Paborsky, et al., "Mammalian cell transient expression of tissue factor for the production of antigen," Protein Engineering, 3(6): 547-553 (1990).
Pinkert, et al., "An albumin enhancer located 10 kb upstream functions along with its promoter to direct efficient, liver-specific expression in transgenic mice," Genes & Development, 1: 268-276 (1987).
Presta, et al., "Humanization of an Antibody Directed Against IgE," The Journal of Immunology, 151: 2623-2632 (1993).
Queen, et al , "Immunoglobulin Gene Transcription is Activated by Downstream Sequence Elements," Cell, 33: 741-748 (1983).
Reichmann, et al., "Reshaping human antibodies for therapy," Nature, 332: 323-327 (1988).
Scallon, et al., "Functional Comparisons of Different Tumour Necrosis Factor Receptor/IgG Fusion Proteins," Cytokine, 7(8): 759-770 (1995).
Schultz, et al., "Expression and secretion in yeast of a 400-kDa envelope glycoprotein derived from Epstein-Barr virus," Gene, 54: 113-123 (1987).
Seed, et al., "An LFA-3 cDNA encodes a phospholipid-linked membrane protein homologous to its receptor CD2," Nature, 329: 840-842 (1987).
Sims, et al., "A Humanized CD18 Antibody Can Block Function without Cell Destruction," The Journal of Immunology, 151(4): 2296-2308 (1993).
Skinner, et al., "Use of the Glu-Glu-Phe C-terminal Epitope for Rapid Purification of the Catalytic Domain of Normal and Mutant *ras* GTPase-activating Proteins," The Journal of Biological Chemistry, 266(22): 14163-14166 (1991).
Smith, et al., "Single-step purification of polypeptides expressed in *Escherichia coli* as fusions with glutathione S-transferase," Gene, 67: 31-40 (1988).
Studier, et al., "Use of T7 RNA Polymerase to Direct Expression of Cloned Genes," *Gene Expression Technology: Methods in Enzymology 185*, Academic Press, San Diego, 60-89 (1990).
Taylor, et al., "Human immunoglobulin transgenes undergo rearrangement, somatic mutation and class switching in mice that lack endogenous IgM," International Immunology, 6(4): 579-591 (1994).
Taylor, et al., "A transgenic mouse that expresses a diversity of human sequence heavy and light chain immunoglobulins," Nucleic Acids Research, 20(23): 6287-6295 (1992).

(56) References Cited

OTHER PUBLICATIONS

Thomas, et al., "Site-Directed Mutagenesis by Gene Targeting in Mouse Embryo-Derived Stem Cells," Cells, 51: 503-512 (1987).

Tuaillon, et al., "Human immunoglobulin heavy-chain minilocus recombination in transgenic mice: Gene-segment use in μ and γ transcripts," Proceedings of the National Academy of Science USA, 90: 3720-3724 (1993).

Verhoeyen, et al., "Reshaping Human Antibodies: Grafting an Antilysozyme Activity," Science, 239: 1534-1536 (1988).

Wada, et al., "Codon usage tabulated from the GenBank genetic sequence data," Nucleic Acids Research, 20: 2111-2118 (1992).

Weintraub, et al., "Anti-sense RNA as a molecular tool for genetic analysis," Trends in Genetics, 1(1): 22-25 (1985).

Wilmut, et al., "Viable offspring derived from fetal and adult mammalian cells," Nature, 385: 810-813 (1997).

Winoto, et al., "A novel, inducible and T cell-specific enhancer located at the 3' end of the T cell receptor a locus," The EMBO Journal, 8(3): 729-733 (1989).

\* cited by examiner

```
           signal      signal                                                        J-C
           intron      sequence                              J1/J2/J4/J5             intron
                       IleGlnAla                             GlyThrLeuValThrValSerSer
  p1628    ..CACAG/GTATACAGGCCT..[irrelevant seq]..GGTACCTTAGTCACCGTCTCCTCAG/GTAA..
                   BstZ17 StuI                            KpnI J6
                                                                Thr
  p1861    ..CACAG/GTATACAGGCCT..[irrelevant seq]..GGTACCAC_GTCACCGTCTCCTCAG/GTAA..

J3
                                                                Met
  p2875    ..CACAG/GTATACAGGCCT..[irrelevant seq]..GGTACCATGGTCACCGTCTCCTCAG/GTAA..
```

VECTORS, HOST CELLS, AND METHODS OF PRODUCTION AND USES

CROSS-REFERENCE TO RELATED APPLICATIONS

This application is a US National Stage of International Application Number PCT/US2008/081090, with international filing date of 24 Oct. 2008, which claims priority to U.S. Provisional Application No. 60/982,814, filed 26 Oct. 2007. The entire contents of each of the aforegoing applications is incorporated herein by reference in their entireties.

FIELD OF THE INVENTION

The present invention relates to vectors and plasmids directing expression of an antibody, host cells, and methods of making and using thereof, including specific vector enhancer and promoter sequences and their interaction with host cell transcription factors.

BACKGROUND

Antibody molecules consist of a combination of two heavy (H) chain and two light (L) chain polypeptides. Each heavy and light chain comprises a constant region containing the CL, CH1, hinge region, CH2, and CH3 regions, and a variable region containing the hypervariable regions (complement determining regions (CDRs)); the CDRs control the antibody's antigen-binding characteristics. The two heavy chains are joined to each other and the light chains in a Y-shaped structure via disulfide bridges such that the variable regions of the light chains ($V_L$) and heavy chains ($V_H$) are located next to each other.

To generate antibodies, conventional hybridoma techniques have been used in which clones of hybrid cells expressing genes coding for the light and heavy chains of an antibody molecule are obtained by immunization with an antigen molecule. This technique necessitates the fusion of cells of lymphocytic origin, containing the genes for antibody formation and cells forming immortal lines. The cells carrying the genes in question are generally obtained by random creation of libraries of circulating cells, and screening of the hybridomas with an antigen-antibody reaction after the hybridoma clones are multiplied and cultured. This technique can be uncertain and laborious with limited yield of antibodies, and is limited in application to non-human (e.g., mouse) antibody production.

In addition, monoclonal antibodies and their fragments can be expressed in various host systems, such as *E. coli*, yeast, and mammalian host cells. In general, a mammalian expression vector will contain (1) regulatory elements, usually in the form of viral promoter or enhancer sequences and characterized by a broad host and tissue range; (2) a "polylinker" sequence, facilitating the insertion of a DNA fragment within the plasmid vector; and (3) the sequences responsible for intron splicing and polyadenylation of mRNA transcripts. This contiguous region of the promoter-polylinker-polyadenylation site is commonly referred to as the transcription unit. The vector will likely also contain (4) a selectable marker gene(s) (e.g., the β-lactamase gene), often conferring resistance to an antibiotic (such as ampicillin), allowing selection of initial positive transformants in *E. coli*; and (5) sequences facilitating the replication of the vector in both bacterial and mammalian hosts.

Unlike most genes that are transcribed from continuous genomic DNA sequences, antibody genes are assembled from gene segments that may be widely separated in the germ line. In particular, heavy chain genes are formed by recombination of three genomic segments encoding the variable (V), diversity (D) and joining (J)/constant (C) regions of the antibody. Functional light chain genes are formed by joining two gene segments; one encodes the V region and the other encodes the J/C region. Both the heavy chain and κ light chain loci contain many V gene segments (estimates vary between 100 s and 1000 s) estimated to span well over 1000 kb. The λ locus is, by contrast, much smaller and has been shown to span approximately 300 kb on chromosome 16 in the mouse. It consists of four joining/constant region gene segments and two variable gene segments. Recombination resulting in functional genes occurs predominantly between $V_1$ and either $J_1/C_1$ or $J_3/C_3$ elements or between $V_2$ and $J_2/C_2$ elements ($J_4/C_4$ is a pseudogene), although recombinations between $V_2$ and $J_3/C_3$ or $J_1/C_1$ are seen very rarely.

An example of a mammalian expression vector is CDM8. The transcription unit of CDM8 is composed of a chimeric promoter (the human cytomegalovirus AD169 constitutive promoter fused to the T7 RNA polymerase promoter), a polylinker region and the SV40 small tumor (t) antigen splice and early region polyadenylation signals derived from pSV2. The human cytomegalovirus (HCMV) promoter is expressed in a variety of mammalian cell types, while the T7 bacteriophage DNA-dependent RNA polymerase promoter can drive in vitro cell-free transcription/translation of cloned inserts. This particular promoter fusion allows initial experiments to be conducted within the confines of the host mammalian cell type, while further analysis and utilization of the cloned insert may potentially be carried out in an in vitro "cell-free" transcription/translation system. The constitutively expressed HCMV promoter has also been utilized in other mammalian expression vectors besides CDM8. Origins of replication in CDM8 include (1) πVX (allowing e.g., replication in *E. coli*) (2) SV40 origin (e.g., allowing replication in a variety of COS cell types) (3) polyoma origin (e.g., allowing replication in polyoma virus transformed mouse fibroblasts) and (4) the bacteriophage M13 origin (e.g., allowing generation of single-stranded template for DNA sequence analysis and/or oligonucleotide site-directed mutagenesis).

Furthermore, CDM8 carries the supF gene for selection in *E. coli*. In this antibiotic selection system, a CDM8-based plasmid construction is transformed into a specialized *E. coli* strain containing an episome carrying genes encoding resistance to the antibiotics, ampicillin and tetracyline. However, both genes contain chain termination ("nonsense" codon) point mutations inactivating the resistance phenotype. The supF gene product, a nonsense suppressor tRNA, restores the resistant phenotype for each antibiotic. Therefore, selection is based on growth of the specialized episomal-carrying *E. coli* strain on media containing ampicillin and tetracycline. Colonies exhibiting this phenotype are supposedly transformed with the CDM8-based plasmid construction.

The CDM8 vector is compatible with COS cell lines as well as cell lines transformed with the polyoma virus. COS cell lines are African green monkey CV1 cells transformed with an origin-defective SV40 mutant virus. The COS cells produce the large T antigen, which is required in trans to promote replication of SV40 or plasmid constructions, such as CDM8, which contain the respective cis-acting sequences initiating viral replication. Therefore, COS cells transfected with a CDM8-based construction will support replication of the plasmid, resulting in increased plasmid copy number and a transient overexpression of the gene of interest.

The major use of CDM8 is cDNA expression cloning and overproduction of specific proteins in a mammalian in vitro expression system. Expression cloning takes on various forms depending on the mode of detection utilized to identify the cDNA of interest; however, the initial step consists of isolating mRNA and synthesizing double-stranded deoxyribonucleic acid copies of the mRNA population (cDNAs). These cDNAs must be efficiently ligated to a plasmid or bacteriophage DNA cloning vector and transferred to the appropriate host prior to library screening and analysis. The CDM8 vector contains two BstXI restriction sites, making it amenable to the "adaptor" linker procedure of ligating cDNAs to the vector, i.e., the use of DNA fragments blunt ended at one end (and therefore compatible for ligation with the blunt ended cDNA) but containing a non-palindromic overhang (sticky end) on the other end (in this instance, compatible for ligation with BstXI digested vector DNA, but not with other cDNAs).

Another example of a mammalian expression vector is pCMX. This vector contains (1) the immediate early promoter of HCMV, (2) an SV40 RNA splice/polyadenylation sequence, (3) an SV40 origin of replication, (4) a pBR322 origin of replication and (5) a selectable marker conferring resistance to an antibiotic, such as the .beta.-lactamase gene conferring resistance to the antibiotic ampicillin. The pCMX vector can also be used for the transient expression of a cloned DNA sequence in transfected COS cells. Control of transcription of both rearranged heavy and .kappa. light chain genes depends both on the activity of a tissue specific promoter upstream of the V region and a tissue specific enhancer located in the J-C intron. These elements act synergistically. Also, a second B-cell specific enhancer has been identified in the .kappa. light chain locus. This further enhancer is located 9 kb downstream of C.sub.kappa.

One such mammalian host system used to produce antibodies is a mouse myeloma host cell that has been transfected with cloned DNA encoding the desired antibody. Such "recombinant monoclonal antibodies" are often distinct from hybridoma-derived monoclonal antibodies for which the DNA has not been cloned and for which the cells producing the monoclonal antibody are derived by immortalizing a natural monoclonal antibody-producing cell isolated from an animal. The heavy and light chain immunoglobulin (Ig) genes being expressed in hybridoma cells are under the control of the natural endogenous promoter that had always been linked to the particular variable region sequence being expressed as opposed to the promoter contained in the recombinant vector.

In recombinant production, the monoclonal antibody sequence to be cloned must be ligated into an appropriate vector after restriction enzyme treatment of the vector. This task can be difficult and imprecise as the process of incorporating the antibody nucleotide sequence(s) into an expression vector or plasmid is complex.

However, by cloning the monoclonal antibody DNA sequences prior to preparing transfected cell-derived monoclonal antibodies, recombinant DNA methods can be used to replace the natural endogenous promoter for an Ig gene with any promoter of choice. A primary reason for changing a promoter is to realize higher monoclonal antibody production levels.

Promoter sequences, in conjunction with downstream enhancer sequences, are responsible for driving transcription (i.e., RNA synthesis) of the heavy and light chain genes in the transfected cells by binding to specialized nuclear proteins called transcription factors. It has become apparent that there are fewer sites for transcription factor binding in an Ig promoter than there are in an Ig enhancer; however, the fact that there is sequence variability among promoters but only a single copy of an enhancer sequence makes it highly likely that there is functional variability among Ig promoters. One promoter may be "strong," i.e., efficient at binding a favorable combination of transcription factors that leads to high levels of monoclonal antibody RNA synthesis, whereas another promoter may be "weak," due to having a different DNA sequence. Since each of the more than 200 variable region HC genes and the more than 200 variable region LC genes in an Ig repertoire has its own naturally linked promoter, and it is likely that no two promoters have identical sequences, the many different Ig promoters are likely to vary significantly with respect to how well they drive transcription.

Ig promoters are only functional in lymphoid-type host cells, such as T cells and B cells (and myeloma cells), due to their requirement for Ig gene-specific transcription factors (for example, Oct-2 and OBF-1) not expressed in other cell types. In addition, even lymphoid cell-specific transcription factors may be expressed only at particular stages of cellular differentiation such that optimal expression may depend on matching the differentiation state of the host cell line with the appropriate sequence motifs in the Ig gene promoters. Although the host cell specificity of Ig promoters may be seen as a minor disadvantage for expression of the monoclonal antibody in a non-lymphoid host cell, the large assortment of HC and LC promoters affords a chance to identify and perhaps further optimize strong promoters that can be incorporated into lymphoid cell-specific vectors.

Expression of monoclonal antibodies behind a strong promoter increases the chances of identifying high-producing cell lines and obtaining higher yields of monoclonal antibodies. Consequently, Ig vectors with strong promoters are highly desirable for expressing any monoclonal antibody of interest. In addition, vectors with unique DNA cloning sites downstream of strong promoters would have an added convenience.

Accordingly, there is a need for new vectors and plasmids useful for expression of antibodies that simplify ligation techniques and enable customization of enhancer and promoter sequences in order to increase antibody production.

SUMMARY OF THE INVENTION

The present invention relates to recombinant expression vectors and plasmids comprising restriction sites for cloning of various antibodies. In another embodiment, the invention provides expression control sequences in the vector, such as enhancer and promoter sequences, that can be customized related to the antibody gene to be cloned and transcribed and the host cell type to be used, in order to drive transcription efficiently. The present invention also comprises isolated host cells, e.g., mammalian and non-mammalian cells, containing such a vector or plasmid. The invention further provides methods for producing an antibody by culturing, in a suitable medium, a host cell containing a recombinant expression vector of the invention such that the antibody is produced.

In another embodiment, the invention comprises a method for identifying, modulating, and/or determining the interaction between host cell transcription factors and promoter and enhancer sequences of an expression vector. This interaction drives the transcription process. The transcription factors and promoter and enhancer sequences can be customized to improve their affinity for or binding to each other, which can increase the yield and efficiency of the transcription process.

The present invention further provides any invention described herein.

DESCRIPTION OF THE INVENTION

Figures 1A, 1B:
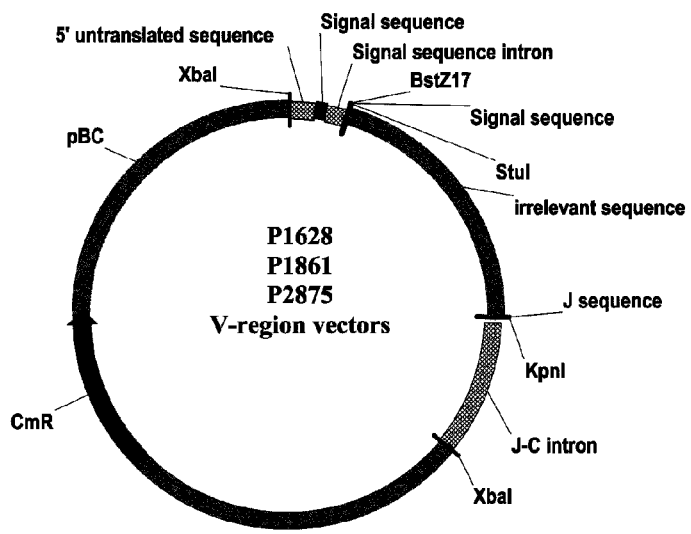
FIG. 1A is a schematic depiction of the vector map for HC1 expression vector.
FIG. 1B shows the differences between the HC1 expression vectors.

The following definitions are set forth to illustrate and define the meaning and scope of various terms used to describe the invention herein.

An "activity," a biological activity, and a functional activity of a polypeptide refer to an activity exerted by a protein or polypeptide in response to its specific interaction with another protein or molecule as determined in vivo, in situ, or in vitro, according to standard techniques. Such activities can be a direct activity, such as an association with or an enzymatic activity on a second protein, or an indirect activity, such as a cellular process mediated by interaction of the protein with a second protein or a series of interactions as in intracellular signalling or the coagulation cascade.

An "antibody" includes any polypeptide or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion, fragment or variant thereof. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. For example, antibody fragments include, but are not limited to, Fab (e.g., by papain digestion), Fab' (e.g., by pepsin digestion and partial reduction) and F(ab')2 (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, et al., eds., Current Protocols in Immunology, John Wiley & Sons, Inc., NY (1994-2001); Colligan et al., Current Protocols in Polypeptide Science, John Wiley & Sons, NY, N.Y., (1997-2001)).

"Chimeric" or "fusion" molecules are nucleic acids or polypeptides that are created by combining one or more of polynucleotides (or their parts) with additional nucleic acid sequence(s). Such combined sequences may be introduced into an appropriate vector and expressed to give rise to a chimeric or fusion polypeptide.

"Complement of" or "complementary to" a nucleic acid sequence of the invention refers to a polynucleotide molecule having a complementary base sequence and reverse orientation as compared to a first polynucleotide.

"Fragment" is a variant polypeptide having an amino acid sequence that is entirely the same as part but not all of any amino acid sequence of a polypeptide or a variant polynucleotide having a nucleic acid sequence that is entirely the same as part but not all of any nucleic acid sequence of any polynucleotide. Fragments can include, e.g., truncation polypeptides having a portion of an amino acid sequence, or of variants thereof, such as a continuous series of residues that includes a heterologous amino- and/or carboxy-terminal amino acid sequence. Degradation forms of the polypeptides produced by or in a host cell are also included. Other exemplary fragments are characterized by structural or functional attributes, such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions, and high antigenic index regions.

Further exemplary fragments include an isolated polypeptide comprising an amino acid sequence having at least 15, 20, 30, 40, 50 or 100 contiguous amino acids from a full-length amino acid sequence, or an isolated polypeptide comprising an amino acid sequence having at least 15, 20, 30, 40, 50 or 100 contiguous amino acids truncated or deleted from the full-length amino acid sequence. Fragments also include isolated polynucleotides having similar sizes and characteristics.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990). The BLAST X program is publicly available from NCBI and other sources (BLAST Manual, Altschul, S., et al., NCBINLM NIH Bethesda, Md. 20894: Altschul, S., et al., J. Mol. Biol. 215: 403-410 (1990). The well-known Smith Waterman algorithm may also be used to determine identity.

Preferred parameters for polypeptide sequence comparison include the following:
(1) Algorithm: Needleman and Wunsch, J. Mol. Biol. 48:443-453 (1970) Comparison matrix: BLOSSUM62 from Hentikoff and Hentikoff, Proc. Natl. Acad. Sci, USA. 89:10915-10919 (1992)
Gap Penalty: 12
Gap Length Penalty: 4

A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:
(1) Algorithm: Needleman and Wunsch, J. Mol. Biol. 48:443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid sequence comparisons.

By way of example, a polynucleotide sequence may be identical to a sequence, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:

$n_n \leqsim x_n - (x_n \cdot y)$, wherein $n_n$ is the number of nucleotide alterations, $x_n$ is the total number of nucleotides in the sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding a polypeptide may create nonsense, missense or frameshift mutations in this coding sequence and thereby alter the polypeptide encoded by the polynucleotide following such alterations. Similarly, a polypeptide sequence may be identical to a reference sequence, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the sequence by the numerical percent of the respective percent identity (divided by 100) and then subtracting that product from the total number of amino acids in the sequence, or:

$n_a \leqsim x_a - (x_a \cdot y)$, wherein $n_a$ is the number of amino acid alterations, $x_a$ is the total number of amino acids in the sequence, and y is for instance 0.70 for 70%, 0.80 for 80%, 0.85 for 85% etc., and wherein any non-integer produce of $x_a$ and y is rounded down to the nearest integer prior to subtracting it from $x_a$.

"Nucleic acids" are polymers of nucleotides, wherein a nucleotide comprises a base linked to a sugar which sugars are in turn linked one to another by an interceding at least bivalent molecule, such as phosphoric acid. In naturally occurring nucleic acids, the sugar is either 2'-deoxyribose (DNA) or ribose (RNA). Unnatural poly- or oliogonucleotides contain modified bases, sugars, or linking molecules, but are generally understood to mimic the complementary nature of the naturally occurring nucleic acids after which they are designed. An example of an unnatural oligonucleotide is an antisense molecule composition that has a phosphorothioate backbone. An "oligonucleotide" generally refers to nucleic acids having less than 30 nucleotides.

A "polypeptide" is a polymer of amino acid residues joined by peptide bonds, and a peptide generally refers to amino acid polymers of 12 or less residues. Peptide bonds can be produced naturally as directed by the nucleic acid template or synthetically by methods well known in the art.

A "protein" is a macromolecule comprising one or more polypeptide chains. A protein may further comprise substituent groups attached to the side groups of the amino acids not involved in formation of the peptide bonds. Typically, proteins formed by eukaryotic cell expression also contain carbohydrates. Proteins are defined herein in terms of their amino acid sequence or backbone and substituents are not specified, whether known or not.

The term "receptor" denotes a molecule having biological activity resulting from interaction with a specific ligand or binding partner. Cell membrane bound receptors are characterized by an extracellular ligand-binding domain, one or more membrane spanning or transmembrane domains, and an intracellular effector domain that is typically involved in signal transduction. Ligand binding to cell membrane receptors causes changes in the extracellular domain that are communicated across the cell membrane, direct or indirect interaction with one or more intracellular proteins, and alters cellular properties, such as enzyme activity, cell shape, or gene expression profile. Receptors may also be untethered to the cell surface and may be cytosolic, nuclear, or released from the cell altogether. Non-cell associated receptors are termed soluble receptors.

All publications or patents cited herein are entirely incorporated herein by reference, whether or not specifically designated accordingly, as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Recombinant Expression Vectors and Host Cells

The invention provides vectors, preferably, expression vectors, containing a nucleic acid encoding a specific polypeptide, for example, an antibody that binds to a cytokine (e.g., IL-1, IL-6, IL-12, etc.) or may be used to obtain plasmids containing various antibody HC or LC genes or portions thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, e.g., expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). In addition, the regulatory sequence is optimized based on the host cell characterisitics, i.e., transcription factors.

The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion and chimeric proteins or peptides, encoded by nucleic acids as described herein.

The recombinant expression vectors of the invention can be designed for expression of a polypeptide in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

To assist in affinity purification, various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol, 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering 3(6):547-553 (1990)). Other tag polypeptides include the Flag-peptide (Hopp et al., Bio Technology, 6:1204-1210 (1988)); the KT3 epitope peptide (Martin et al., Science, 255:192-194 (1992)); an .alpha.-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)). A preferred tag is the FLAG tag.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression in *E. coli* is to express the protein in host bacteria with an impaired capacity to proteolytically cleave the recombinant protein (Gottesman, *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al. (1987) *EMBO J.* 6:229-234), pMFa (Kurjan and Herskowitz, (1982) *Cell* 30:933-943), pJRY88 (Schultz et al. (1987) *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells, see chapters 16 and 17 of Sambrook et al., supra.

In another embodiment, the recombinant mammalian expression vector is capable of directing expression of the nucleic acid, preferentially in a particular cell type, such as lymphoma cells (e.g., mouse myeloma cells). In specific cell types, tissue-specific regulatory elements are used to express the nucleic acid. Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular, promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, by the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule cloned into the expression vector in an antisense orientation. That is, the DNA molecule is operably linked to a regulatory sequence in a manner that allows for expression (by transcription of the DNA molecule) of an RNA molecule that is antisense to the mRNA encoding a polypeptide. Regulatory sequences operably linked to a nucleic acid cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub et al. (*Reviews—Trends in Genetics*, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells). A number of suitable mammalian host cell lines capable of expressing intact glycosylated polypeptides have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org).

Expression vectors for these cells can include one or more of the following expression control sequences, a promoter, an enhancer, and/or processing information sites, such as ribosome binding sites, RNA splice sites, polyadenylation sites, and transcriptional terminator sequences (See, e.g., Ausubel et al., supra; Sambrook, et al., supra).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as, chloramphenicol, tetracyclines, gentamycin, kanamycin, ampicillin, G418, hygromycin, methotrexate, etc. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide. Accordingly, the invention further provides methods for producing a polypeptide using the host cells of the invention. In one embodiment, the method comprises culturing the host cell of the invention (into which a recombinant expression vector encoding a polypeptide has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which at least one sequence encoding a polypeptide has been introduced. Such host cells can then be used to create non-human transgenic animals in which exogenous sequences encoding a polypeptide have been introduced into their genome or homologous recombinant animals in which endogenous sequences encoding a polypeptide have been altered. Such animals are useful for studying the function and/or activity of the polypeptide and for identifying and/or evaluating modulators of polypeptide activity. As used herein, a "transgenic animal" is a non-human animal, preferably, a mammal, more preferably, a rodent, such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide to particular cells. Methods for generating transgenic animals via embryo manipulation and microinjection, particularly, animals such as mice, have become conventional in the art and are described, for example, in U.S. Pat. Nos. 4,736,866, 4,870,009, and 4,873,191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create a homologous recombinant animal, a vector is prepared which contains at least a portion of a gene encoding a polypeptide into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication NOS. WO 90/11354, WO 91/01140, WO 92/0968, and WO 93/04169.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813 and PCT Publication Nos. WO 97/07668 and WO 97/07669.

Antibodies

The present invention further includes, but is not limited to, methods of using nucleic acids and polypeptides encoded thereby to make antibodies and anti-idiotype antibodies, including diagnostic and therapeutic compositions, methods and devices. Such antibodies optionally further affect a specific ligand, such as but not limited to, where such antibody modulates, decreases, increases, antagonizes, agonizes, mitigates, alleviates, blocks, inhibits, abrogates and/or interferes with at least one protein activity or binding, or with receptor activity or binding, in vitro, in situ and/or in vivo. As a non-limiting example, a suitable antibody, specified portion or variant can bind at least one protein, or specified portions, variants or domains thereof. A suitable antibody, specified portion, or variant can also optionally affect at least one of protein activity or function, such as but not limited to, RNA, DNA or polypeptide synthesis, protein release, receptor signaling, membrane cleavage, protein activity, protein production and/or synthesis. Antibodies useful in the methods and compositions of the present invention can optionally be characterized by high affinity binding to their antigens and, optionally and preferably, having low toxicity.

As used herein, an "antibody," and the like include any polypeptide or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion, fragment or variant thereof, or at least one portion of a receptor or binding polypeptide, which can be incorporated into an antibody.

Antibodies can include one or more of at least one CDR, at least one variable region, at least one constant region, at least one heavy chain (e.g., g1, g2, g3, g4, m, a1, a2, d, e), at least one light chain (e.g., kappa and lambda), or any portion or fragment thereof, and can further comprise interchain and intrachain disulfide bonds, hinge regions, glycosylation sites that can be separated by a hinge region, as well as heavy chains and light chains. Light chains typically have a molecular weight of about 25 Kd and heavy chains typically range from 50K-77 Kd. Light chains can exist in two distinct forms or isotypes, kappa (k) and lambda (l), which can combine with any of the heavy chain types. All light chains have at least one variable region and at least one constant region. The IgG antibody is considered a typical antibody structure and has two intrachain disulfide bonds in the light chain (one in variable region and one in the constant region), with four in the heavy chain, and such bond encompassing a peptide loop of about 60-70 amino acids comprising a "domain" of about 110 amino acids in the chain. IgG antibodies can be characterized into four classes, IgG1, IgG2, IgG3 and IgG4. Each immunoglobulin class has a different set of functions. The following table summarizes the Physicochemical properties of each of the immunoglobulin classes and subclasses.

antibody preparation. The full-length polypeptide or protein can be used or, alternatively, the invention provides antigenic peptide fragments for use as immunogens. The antigenic peptide comprises at least 8 (preferably 10, 15, 20, or 30 or more) amino acid residues of a protein's sequence and encompasses an epitope of the protein such that an antibody raised against the peptide forms a specific immune complex with the protein.

An immunogen typically is used to prepare antibodies by immunizing a suitable (i.e., immunocompetent) subject, such as a rabbit, goat, mouse, or other mammal or vertebrate. An appropriate immunogenic preparation can contain, for example, recombinantly expressed or chemically synthesized polypeptide. The preparation can further include an adjuvant, such as Freund's complete or incomplete adjuvant, or a similar immunostimulatory agent.

Antibody-producing cells can be obtained from the peripheral blood or, preferably, the spleen or lymph nodes of humans or other suitable animals that have been immunized with the immunogen of interest. Any other suitable host cell can also be used for expressing heterologous or endogenous nucleic acid encoding an antibody, specified fragment or variant thereof. The fused cells (hybridomas) or recombinant cells can be isolated using selective culture conditions or other suitable known methods, and cloned by limiting dilution or cell sorting, or other known methods. Cells that pro-

| Property | IgG1 | IgG2 | IgG3 | IgG4 | IgM | IgA1 | IgA2 | SIgA | IgD | IgE |
|---|---|---|---|---|---|---|---|---|---|---|
| Heavy Chain | γ1 | γ1 | γ1 | γ1 | μ | α1 | α2 | α1α2 | δ | ε |
| Mean Serum conc. (mg/ml) | 9 | 3 | 1 | 0.5 | 1.5 | 3.0 | 0.5 | 0.05 | 0.03 | 0.00005 |
| Sedimentation constant | 7s | 7s | 7s | 7s | 19s | 7s | 7s | 11s | 7s | 8s |
| Mol. Wt. ($\times 10^3$) | 146 | 146 | 170 | 146 | 970 | 160 | 160 | 385 | 184 | 188 |
| Half Life (days) | 21 | 20 | 7 | 21 | 10 | 6 | 6 | ? | 3 | 2 |
| % intravascular distribution | 45 | 45 | 45 | 45 | 80 | 42 | 42 | Trace | 75 | 50 |
| Carbohydrate (%) | 2-3 | 2-3 | 2-3 | 2-3 | 12 | 7-11 | 7-11 | 7-11 | 9-14 | 12 |

The following table summarizes non-limiting examples of antibody effector functions for human antibody classes and subclasses.

| Effector function | IgG1 | IgG2 | IgG3 | IgG4 | IgM | IgA | IgD | IgE |
|---|---|---|---|---|---|---|---|---|
| Complement fixation | + | +/− | ++ | − | ++ | − | − | − |
| Placental transfer | + | +/− | + | + | − | − | − | − |
| Binding to Staph A | +++ | +++ | − | +++ | − | − | − | − |
| Binding to Strep G | +++ | +++ | +++ | +++ | − | − | − | − |

+++ = very high; ++ = high; + = moderate; +/− = minimal; − = none; ? = questionable As described below, various methods exist to produce antibodies. Once an antibody is produced by any of these methods, its amino acid and corresponding gene sequences can be identified and, optionally, modified (e.g., optimized, humanized, etc.) such that the antibody can then be produced recombinantly.

For example, a specified polypeptide, or a fragment thereof, can be used as an immunogen to generate antibodies using standard techniques for polyclonal and monoclonal antibody preparation.

duce antibodies with the desired specificity can be selected by a suitable assay (e.g., ELISA).

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like), or heteromyelomas, fusion products thereof, or any cell or fusion cell derived therefrom, or any other suitable cell line as known in the art (see, e.g., www.atcc.org, www.lifetech.com, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Other suitable methods of producing or isolating antibodies of the requisite specificity can be used, including, but not limited to, methods that select recombinant antibody from a peptide or polypeptide library (e.g., but not limited to, bacteriophage, ribosome, oligonucleotide, RNA, cDNA, or the like, display library; e.g., as available from Cambridge antibody Technologies, Cambridgeshire, UK; MorphoSys, Martinsried/Planegg, DE; Biovation, Aberdeen, Scotland, UK; Bioinvent, Lund, Sweden; Dyax Corp., Enzon, Affymax/Biosite; Xoma, Berkeley, Calif.; Ixsys. See, e.g., EP 368,684; PCT/GB91/01134; PCT/GB92/01755; PCT/GB92/002240; PCT/GB92/00883; PCT/GB93/00605; U.S. Ser. No. 08/350,260 (May 12, 1994); PCT/GB94/01422; PCT/GB94/02662; PCT/GB97/01835; (CAT/MRC); WO90/14443; WO90/14424; WO90/14430; PCT/U594/1234; WO92/18619; WO96/07754; (Scripps); EP 614 989 (MorphoSys); WO95/16027 (Bioinvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or polypeptides—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., at the following web sites: www.ncbi.nlm.nih.gov/entrez/query.fcgi; www.atcc.org/phage/hdb.html; www.sciquest.com/; www.abcam.com/; www.antibodyresource.com/onlinecomp.html; www.publiciastate.edu/~pedro/research_tools.html; www.mgen.uni-heidelberg.de/SD/IT/IT.html; www.whfreeman.com/immunology/CH05/kuby05.htm; www.library.thinkquest.org/12429/Immune/Antibody.html; www.hhmi.org/grants/lectures/1996/vlab/; www.path.cam.ac.uk/~nrc7/mikeimages.html; www.antibodyresource.com/; mcb.harvard.edu/BioLinks/Immunology.html.www.immunologylink.com/; pathbox.wustLedu/~hcenter/index.html; www.biotech.ufl.edu/~hcl/; www.pebio.com/pa/340913/340913.html; www.nal.usda.gov/awic/pubs/antibody/; www.m.ehime-u.ac.jp/~yasuhito/Elisa.html; www.biodesign.com/table.asp; www.icnet.uk/axp/facs/davies/links.html; www.biotech.u-fl.edu/~fccl/protocol.html; www.isac-net.org/sites_geo.html; aximtl.imt.uni-marburg.de/~Tek/AEP-Start.html; baserv.uci.kun.nl/~jraats/links1.html; www.recab.uni-hd.de/immuno.bme.nwu.edu/; www.mrc-cpe.cam.ac.uk/imt-doc/public/INTRO.html; www.ibt.unam.mx/vir/N_mice.html; imgt.cnusc.fr:8104/; www.biochem.ucLac.uk/~martin/abs/index.html; antibody.bath.ac.uk/; abgen.cvm.tamu.edu/lab/www.abgen.html; www.unizh.ch/~honegger/AHOseminar/Slide01.html; www.cryst.bbk.ac.uk/~ubcg07s/; www.nimr.mrc.ac.uk/CC/ccaewg/ccaewg.htm; www.path.cam.ac.uk/~nrc7/humanisation/TAHHP.html; www.ibt.unam.mx/vir/structure/stat_aim.html; www.biosci.missouri.edu/smithgp/index.html; www.cryst.bioc.cam.ac.uk/~fmolina/Web-pages/Pept/spottech.html; www.jerini.de/fr_products.htm; www.patents.ibm.com/ibm.html.Kabat et al., Sequences of Polypeptides of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally, part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to, those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567; PCT/: US98/16280; US96/18978; US91/09630; US91/05939; US94/01234; GB89/01334; GB91/01134; GB92/01755; WO90/14443; WO90/14424; and WO90/14430; EP 229246; each entirely incorporated herein by reference, including references cited therein.

Antibodies can also be optionally generated by immunization of a transgenic animal (e.g., mouse, rat, hamster, non-human primate, and the like) capable of producing a repertoire of human antibodies, as described herein and/or as known in the art. Cells that produce an antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. *Nature* 368:856-859 (1994), Taylor et al., *Int. Immunol.* 6(4)579-591 (1994), Green et al, *Nature Genetics* 7:13-21 (1994), Mendez et al., *Nature Genetics* 15:146-156 (1997), Taylor et al., *Nucleic Acids Research* 20(23):6287-6295 (1992), Tuaillon et al., *Proc Natl Acad Sci USA* 90(8)3720-3724 (1993), Lonberg et al., *Int Rev Immunol* 13(1):65-93 (1995) and Fishwald et al., *Nat Biotechnol* 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Antibodies can also be prepared in milk by administering at least one antibody encoding nucleic acid to transgenic animals or mammals, such as goats, cows, horses, sheep, and the like, that produce antibodies in their milk. Such animals can be provided using known methods. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference. Antibodies can additionally be prepared using at least one antibody encoding nucleic acid to provide transgenic plants and cultured plant cells (e.g., but not limited to, tobacco and maize) that produce such antibodies, specified portions or variants in the plant parts or in cells cultured therefrom.

The antibodies can bind antigens with a wide range of affinities ($K_D$). In a preferred embodiment, at least one human monoclonal antibody of the present invention can optionally bind its antigen with high affinity. For example, a human monoclonal antibody can bind human antigen with a $K_D$ equal to or less than about $10^{-7}$ M, such as but not limited to, 0.1-9.9 (or any range or value therein) X $10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

An antibody directed against a polypeptide (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Characteristics of Vectors

The inherent promoters of transfected cell lines with robust monoclonal antibody production capacity were investigated. It was unexpectedly found that good production levels, i.e., greater than about 500 mg/L on a specific productivity basis, were obtained, even with human gene promoters that are recognized by mouse transcription factors in the murine myeloma host cell. The invention provides expression vectors designed for high-level expression of proteins of interest in lymphoid-type cells. Preferred host cells include, for example, mouse myeloma cells, such as Sp2/0, 653, and NS0 cell lines. Proteins of interest include, for example, antibodies or Mimetibody™ constructs. The vectors can be used in a 2-step modular format to enable flexibility in designing the N-terminal and C-terminal ends of the protein of interest.

For example, the invention provides the complete DNA sequence of the HC and LC expression vector backbones into which an antibody gene sequence may be inserted. The vectors have been engineered to enable convenient insertion of various antibody variable region genes. For example, the variable region sequence can encode a monoclonal antibody of interest, such as an antibody for a human interleukin, a growth factor, etc. Additionally, the vectors allow for the replacement of antibody constant regions. Four different expression vectors according to the invention are described below and their maps are depicted schematically in FIGS. 1-4. Their sequences are disclosed in SEQ ID NOS:1-6.

The vector components, which apply to both HC and LC vectors, could include the following:

1. the gene promoter/transcription initiation nucleic acid sequence
2. the 5' untranslated sequences and translation initiation nucleic acid sequences
3. the nucleic acid sequences encoding the signal sequence and the signal amino acid sequence itself
4. intron/exon splice donor sequences for the signal intron and the J-C intron
5. the J-C intron enhancer nucleic acid sequences Perhaps the components most likely to be responsible for the high expression levels obtained without further confirmation are the 1$^{st}$ and 3$^{rd}$ components listed above.

The expression vectors described here can be divided into heavy chain (HC) vectors and light chain (LC) vectors. They can be further divided into variable (V) region vectors (N-terminal part of an Ab) and constant (C) region vectors (C-terminal part of an Ab). The starting material for all HC V region vector engineering work was plasmid p139, a pUC19 plasmid that contains a 5.8 kb EcoRI-EcoRI genomic fragment cloned from C123 hybridoma cells secreting a fully mouse Ab; the fragment contains the promoter and V region part of the HC gene. The starting material for LC V region vector engineering was plasmid p39, a pUC plasmid that contains a 3 kb HindIII-HindIII genomic fragment cloned from C123 hybridoma cells; this fragment contains the promoter and V region part of the LC gene. The engineered vectors derived from p139 and p39 were designed to enable convenient assembly of HC or LC genes suitable for expression in a mammalian host cell in a 2-step process that entails:
1. cloning DNA encoding a sequence of interest between specially-prepared restriction sites in a V region vector.
    a. upon such cloning, the V region coding sequence is positioned immediately downstream of the vector-encoded signal sequence, as well as downstream of part or all of the gene promoter.
2. transferring a fragment that spans the inserted sequence from the V region vector to the C region vector in the proper orientation.
    a. the resulting plasmid constitutes the final expression plasmid suitable for expression in cells.

HC-V Region Vectors p1628, p1861, and p2875

Plasmid p1628 (FIG.; SEQ ID NO:1) is an HC V region vector that provides the transcription initiation site, the translation initiation site, signal sequence, three unique restriction sites (BstZ17, StuI, and KpnI) optionally used for introducing inserts near the C-terminal end of the signal sequence, the C-terminal end of Ab J coding sequence (for human J1, J2, J4, J5), and the 5' end of the J-C intron (FIG. 1A; also see Table 1)—all taken from the heavy chain gene in p139. p1628 was prepared by modifying the precursor plasmid p1540. Plasmids p1861 and p2875 are identical to p1628 except for encoding the C-terminal ends of human J6 and J3, respectively (as shown in FIG. 1B). The amino acid sequence of the signal sequence encoded in p1628, p1861, and p2875 is as follows:

(SEQ ID NO: 7)
Met-Ala-Trp-Val-Trp-Thr-Leu-Leu-Phe-Leu-Met-Ala-

Ala-Ala-Gln-Ser-Ile-Gln-Ala

After introducing a foreign insert between the BstZ17 and KpnI sites, or between the StuI and KpnI sites, the XbaI-XbaI fragment spanning the foreign insert can be transferred into p730, described below, or another vector encoding a different downstream amino acid sequence.

HC-C Region Vector p730

Figure 2:
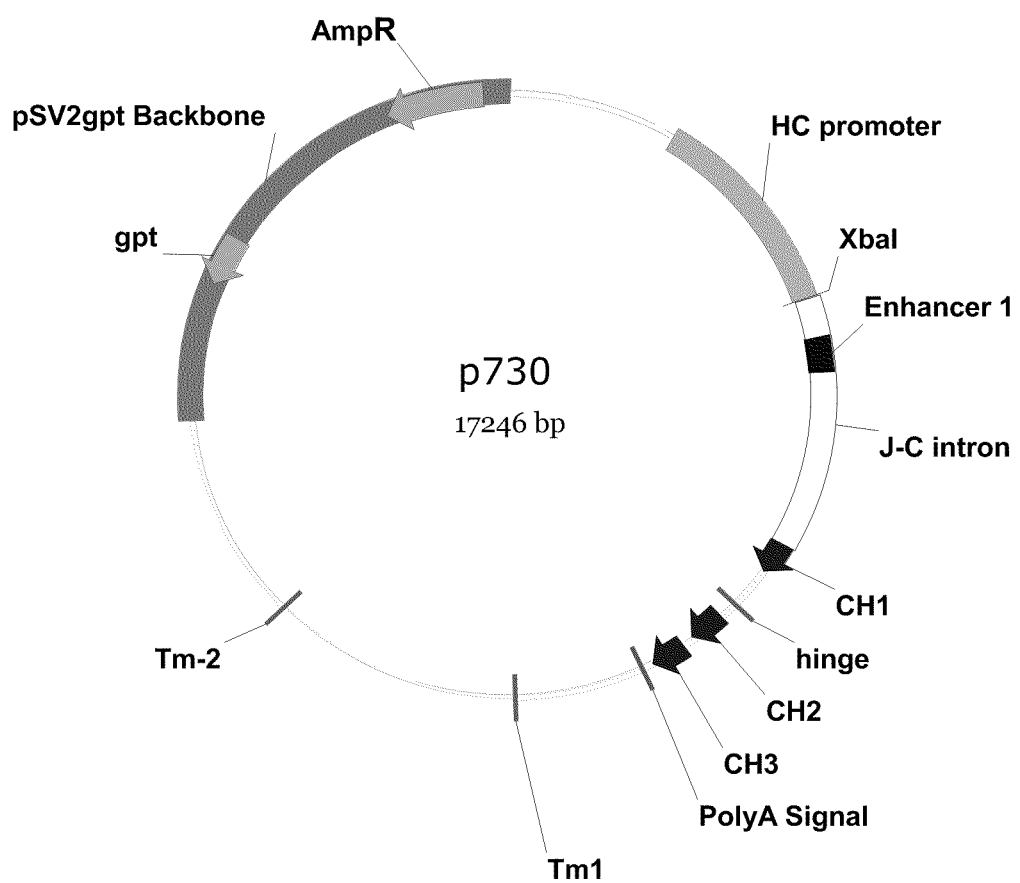
FIG. 2 is a schematic depiction of the vector map for LC1 expression vector.
Figure 3:
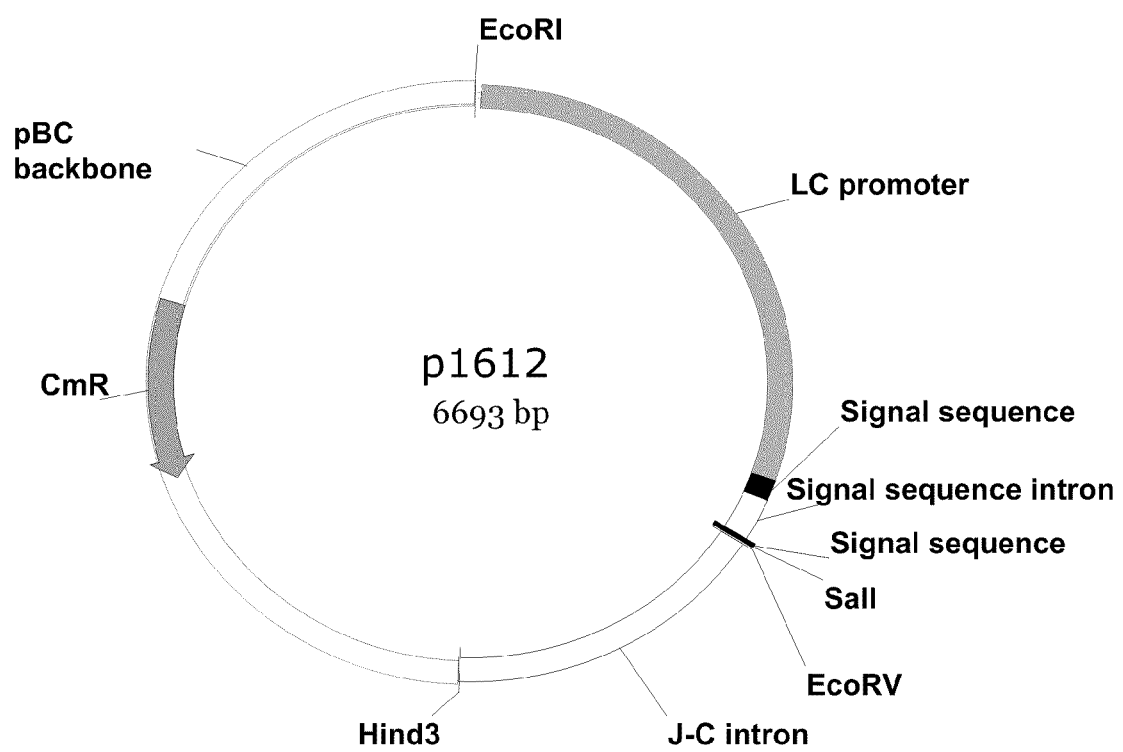
FIG. 3 is a schematic depiction of the vector map for HC2 expression vector.
Figure 4:
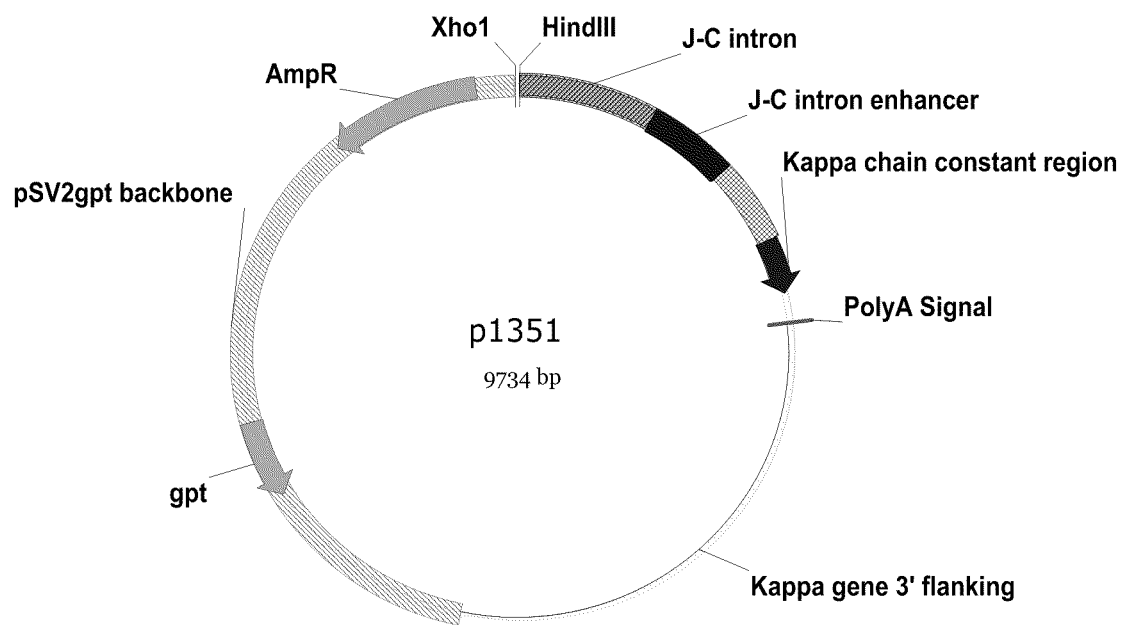
FIG. 4 is a schematic depiction of the vector map for LC2 expression vector.

Plasmid p730 (FIG. 2; SEQ ID NO:2) was designed to accommodate a restriction fragment from p1628, p1861, or p2875 V region vectors in such a way that all components required to assemble a suitable expression plasmid that are not provided in the V region construct are provided in the final p730-based construct (see Table 1). For example, whereas p1628 does not provide the promoter but provides the transcription start site, p730 provides the entire promoter. Also, whereas p1628 does not provide C region coding sequences, p730 does provide a C region coding sequence. Consequently, step 2 of the 2-step process of assembling a fully functional expression plasmid is accomplished by transferring the XbaI-XbaI fragment from the V region construct into the unique XbaI site in p730 and identifying resulting plasmids with the transferred fragment in the appropriate orientation.

LC-V Region Vector p1612

Plasmid p1612 is an LC-V region vector which, unlike the HC-V region vectors described above, provides a complete promoter region, this one derived from the Ab LC gene. It also provides two different unique restriction sites (SalI and EcoRV) for cloning foreign sequences, and a non-critical part of the J-C intron of the Ab LC sequence. Inserts may be introduced either between the SalI and EcoRV sites or into the middle of the EcoRV site. After introducing a foreign insert, the XhoI-HindIII fragment spanning the foreign insert can be transferred into the HC-C vector or another vector encoding a different downstream amino acid sequence. The amino acid sequence of the signal sequence encoded in p1612 is as follows:

(SEQ ID NO: 8)
Met-Gly-Ile-Lys-Met-Glu-Thr-His-Ser-Gln-Val-Phe-

Val-Tyr-Met-Leu-Leu-Trp-Leu-Ser-Gly-Glu-Thr-Phe-

Lys-Ser-Val-<u>Asp</u>-Gly

However, the original LC signal sequence has a Glu instead of an Asp at the 2$^{nd}$ position from the C-terminus (underlined above). The p1612 codon was changed in order to introduce a SalI cloning site; however, the original Glu codon is easily restored upon introducing a foreign insert by appropriate design of the 5' end of the insert. After introducing the foreign inserts into p1612, the XhoI-HindIII fragment spanning the foreign insert can be transferred to p1351, described below, or another vector encoding a different LC constant region.

LC-C Region Vector p1351

Plasmid p1351 is a pSV2gpt-based kappa LC expression vector derived from p95 by cloning a small double-stranded oligonucleotide sequence into the HindIII site of p95 in order to provide a unique XhoI cloning site immediately upstream of a unique HindIII cloning site. The transfer of the XhoI-HindIII fragment from p1612-derived plasmids into p1351 results in a fully-assembled and functional plasmid suitable for expression in lymphoid-type cells. The LC-C vector provides an antibody light chain C region coding sequence.

Vectors of the present invention can be used to express the constant region sequences from human IgG1, IgG2, IgG3, IgG4, IgD, IgE, or IgM, mouse IgG1, IgG2a, IgG2b, or IgG3, or rat IgG1, IgG2a, IgG2b, or IgG2c. Alternatively, vectors of the present invention can be used to express the ΔCH1 versions of the above listed constant region sequences.

Any antibody, immunoglobulin derived protein, fusion protein, other protein, or portion thereof can be substituted for the V region coding sequence in the vectors/plasmids of the present invention, e.g., extracellular domain of a TNF receptor. For such a fusion protein that includes the CH1 domain, some form of LC would be required for secretion out of the cell.

TABLE 1

Vector components provided by V region and C region vectors

| Vector component | HC-V (p1628, p1861, an p2875) | HC-C (p730) | LC-V (p1612) | LC-C (p1351) |
|---|---|---|---|---|
| SEQ ID NO | 1, 5, & 6 | 2 | 3 | 4 |
| Vector backbone | pBC-SK+ | pSV2gpt | pUC19 | pSV2gpt |
| Promoter |  | X |  | X |
| Transcription initiation site | X |  | X |  |
| 5' untranslated sequence | X |  | X |  |
| Signal sequence, signal intron | X |  | X |  |
| Unique restriction sites | X | X | X | X |
| J-C intron | 5' end | 3' end | 5' end | 3' end |
| J-C intron enhancer |  | X |  | X |
| C region coding sequence |  | X |  | X |
| Selectable marker for transfections |  | X |  | X |

| Feature | p1628, p1861, p2875 (SEQ ID NOS: 1, 5, and 6) | p1612 (SEQ ID NO: 3) |
|---|---|---|
| 5' restriction site for transferring from V region to C region vector | 1-6 (XbaI)h | 14-19 (EcoR1) |
| 5' flanking sequence | N.A. | 20-34 |
| Ig gene promoter region | 1-102 (partial) | 35-2034 |
| Coding sequence for N-terminus of signal sequence | 103-148 | 2035-2095 |
| Signal sequence intron | 149-228 | 2096-2272 |
| Coding sequence for C-terminus of signal sequence | 229-239 | 2273-2289 |
| 5' restriction sites for insert | 229-234 (BstZ17) 235-240 (StuI) | 2275-2280 (SalI) |
| Irrelevant "stiffer" sequence | 241-1295 | N.A. |
| 3' restriction site for insert | 1296-1301 (KpnI) | 2284-2289 (EcoRV) |
| Joining segment coding sequence | 1296-1320 | N.A. |
| 5' end of J-C intron | 1321-1862 | 2290-3397 |
| 3' restriction site for transferring from V region to C region vector | 1857-1862 (XbaI) | 3398-3403 (Hind3) |
| pBC backbone | 1863-5173 | 3404-6701 |
| Chloramphenicol resistance coding sequence | 3235-3890 | 4681-5337 |

| | p730 (SEQ ID NO: 2) | p1351 (SEQ ID NO: 4) |
|---|---|---|
| 5' flanking sequence | 1-1492 | N.A. |
| Ig gene promoter region | 1493-3390 (partial) | N.A. |
| 5' restriction cloning site | 3391-3396 (XbaI) | 1-6 (XhoI) |
| 3' restriction cloning site | N.A. | 11-16 (Hind3) |
| 3' end of J-C intron | 3397-5701 | 17-1759 |
| CH1 coding sequence | 5702-5995 | N.A. |
| hinge coding sequence | 6384-6428 | N.A. |
| CH2 coding sequence | 6547-6876 | N.A. |
| CH3 coding sequence | 6973-7292 | N.A. |
| C kappa coding sequence | N.A. | 1760-2082 |
| PolyA signal | 7395-7400 | 2255-2260 |
| 3' flanking sequence | 7401-12697 | 2260-5174 |
| pSV2gpt backbone | 12698-17246 | 5190-9734 |
| gpt selectable marker coding sequence | 13971-14426 | 6445-6900 |
| Amp resistance coding sequence | 16181-17038 | 8655-9512 |

Sequence Analysis of the HC-C Gene Promoter

To define elements in the promoter of the HC gene that could impact gene transcription and be partially responsible for the high antibody expression levels observed in transfected cells, bioinformatic analysis of the 2000-base sequence upstream of the HC translation start codon was performed. This analysis identified sequence motifs recognized by relevant transcription factors (TFs). The most up-to-date TF database, TRANSFAC 7.2 (Matys et al, 2003), was used for the comparison. Then, various matrix and pattern search algorithms were applied to identify relevant sequences. Some of the results were subsequently validated by the relevant literature supporting the conclusion that the synergy and the combination of these TFs may drive high production of antibodies.

Several high-quality, mouse-specific transcription factor models were built with different parameters for a matrix search (Goessling et al., 2001). A mouse lymphocyte transcription factor specific model was also constructed for a matrix search. Additionally, several patch searches for different subsequence lengths (6 bps and above) were performed.

Based on these results, 21 potential mouse TFs and their binding sites were identified (Table 2). Most of these TFs were B lymphocyte-specific. Some of the TFs may be activated during different stages of B cell development. Their activations are also dependent on the presence of other binding sites and the interaction of other factors.

The TRANSFAC database accession codes for these mouse TFs are: T01114 for C/EBPdelta; T01786 for E12 (A7/E2A); T05012 for ELF-1; T00152 for CP2; T01852 for HMG_IY; T00549 for NF-AT; T00215 for muEBP-C2; T00814 for TFE3-S; T01675 for NKx2-5; T00479 for Lyf-1 (Ik-1); T01159 for TFIID; T01575 for STATx; T00402 for IRF; T00017 for C/EBPBeta; T00032 for Ap1; T00273 for Evi-1;

T00930 for LEF-1; T00644 for POU2F1a/Oct-1 and T00702 for PU.1. Six TFs were found to be located 500 bp upstream of the transcription initiation site. These are mouse NF-AT, AP-1, Evi-1, LEF-1, POU2F1a/Oct-1 and PU.1.

TABLE 2

Sequence motifs in the HC-C vector promoter relevant to transcription

| Transcription factor | Position in p730 | Binding site ID | Sequence recognized by TF | Core score | Matrix/patch | Sources/Search methods | Annotation |
|---|---|---|---|---|---|---|---|
| C/EBPdelta | 1779− | V$CEBPDELTA_Q6 | catgatGCAATt | 1 | 0.96 | Immuno/HQ | Expressed ubiquitously, synergistically acting with NF-kappaB |
| E12/A7/E2A | 1890+ | V$E12_Q6 | AgCAGGTgcac | 1 | 0.979 | HQ | Functional redundancy of E2A and E2-2 gene products [5], except mature B cells where E2A products (E12/E47) are found exclusively making mature B cell development E2A-dependent |
| ELF-1 | 1933− | V$ELF1_Q6 | CcTTCCTcttcc | 1 | 0.963 | Immuno | Higher levels in B-cells, regulates transcription of a broad range of genes |
| CP2 | 2054+ | V$CP2_01 | GcacaaCCCAG | 1 | 1 | HQ/patch | Appears to be functionally limiting in nuclear B cell extracts |
| HMG IY | 2307+ | V$HMGIY_Q6 | GGAAAgt | 1 | 0.979 | Immuno | Auxiliary factor for other transcription factors such as NF-kappaB or ATF-2 to optimally assemble into a transcription complex |
| NF-AT | 2480+; 3069+ | V$NFAT_Q6 | tacaGGAAAcat; cactGGAAAgg | 1 | 0.98 | Immuno | Activated T cells |
| MuEBP-C2 | 2609− | MOUSE$IGH_10 | CATGTG | | 100 | Patch | Proteins Binding to Site C2 (muE3) in the Immunoglobulin Heavy-Chain |
| TFE3-S | 2609− | MOUSE$IGH_10 | CATGTG | | 100 | Patch | Expressed in B-cell(from Pro B to Plasma),TFE3-deficient B cells may cause a defect of B cells to respond to signals from T cells |
| Nkx2-5 | 2715+ | V$NKX25_02 | CtTAATTg | 1 | 1 | HQ | Lymph node stroma: TSL-1 |
| Lyf-1(Ik-1) | 2822− | V$LYF1_01 | CtTCCCAaa | 1 | 0.956 | Immuno | Expressed in B (from Progenitor to Plasma) and T cell, lack of Ikarus (LyF-1) activity at the late stages of thymocyte maturation leads to uncontrolled lymphoproliferation |
| TFIID | 2857+ | MOUSE$MBP_04 | TTCAAA | | 100 | patch | Interactive with PU.1, REL |
| STATx | 2876− | V$STAT_01 | ttatGGGAA | 1 | 0.972 | HQ | Expressed in B cell, particularly in GC (germinal center) B cell[10]. Important for IFNy, IL4 signaling etc |
| IRF | 2881− | V$IRF_Q6 | ggaaaTGAAAaccca | 1 | 0.968 | HQ | Expressed in spleen, thymus. mRNA induced by IFN-gamma, STAT-like element |
| C/EBPbeta | 2930− | V$CEBPB_02 | tatttcTGCAAatt | 1 | 0.951 | Immuno | Expressed in lymphocytes from GC B to Plasma. They synergize with NF-kB/rel proteins |
| AP-1 | 2955−; 3080− | V$AP1_Q4; V$AP1_Q2 | gattAGTCAct; ataaAGTCAct | 1 | 0.991 | Immuno/HQ | Interactive with c-Ets-1 and NF-Atp |

TABLE 2-continued

Sequence motifs in the HC-C vector promoter relevant to transcription

| Transcription factor | Position in p730 | Binding site ID | Sequence recognized by TF | Core score | Matrix/patch | Sources/Search methods | Annotation |
|---|---|---|---|---|---|---|---|
| Evi-1 | 3282+ | V$EVI1_05 | AgatAAGATaa | 1 | 1 | HQ | involved in myeloid transformation |
| LEF-1 | 3325+; 2703- | MOUSE$ECADH_04 | CTTTGTA;tcC TTTGaac | 1 | 100 | Immuno/HQ/Patch | potent activator in pre-B cells, T lymphocytes |
| Pou2F1a (Oct-1) | 3384- | MOUSE$IGH_44 | ATTTGCAT | | 100 | Patch | DNA-binding is reduced by GR in a ligand-dependent manner |
| PU.1 | 3395-; 1934- | MOUSE$GSHPX1_01 | CTTCTC;CTT CCtct | 1 | 100 | Patch/immuno | Expressed in B-cell from Progenitor to GC B. No B cells if it is deficient |

Sequence Analysis of the LC-V Gene Promoter

The LC gene promoter region was analyzed by the same methods, which yielded a list of 14 potential mouse transcription factors and their binding sites (Table 3). The TRANSFAC database accession codes for these TFs are: T00702 for PU.1; T00814 for TFE3-S; T00215 for muEBP-C2; T00402 for IRF; T00549 for NF-AT; T00613 for NF-Y; T00032 for Ap1; T01675 for NKx2-5; T00278 for YY1; T00930 for LEF-1; T00479 for Lyf-1 (Ik-1); T00111 for c-Ets-1; T01397 for c-Ets-2 and T00644 for POU2F1a (Oct-1). Among them, AP-1, YY1, LEF-1, Lyf-1, c-Ets-1, c-Ets-2 and POU2F1a (Oct-1) were found to be located in the 500 bps upstream of the transcription start site.

TABLE 3

Sequence motifs in the LC-V promoter relevant to transcription

| Transcription factor | Position in p1612 | Binding site ID | Sequence recognized by TF | Core score | Matrix/patch | Sources/Search method | Annotation |
|---|---|---|---|---|---|---|---|
| PU.1 | 356-; 239+ | V$PU1_Q6 | CTTCCtca; aggGGAAG | 1 | 0.984 | Immuo/patch | Expressed in B-cell from Progenitor to GC B. No B cells if it is deficient |
| TFE3-S | 412+; 1294+ | MOUSE$IGH_10 | CATGTG | | 100 | Patch | Expressed in B-cell (from Pro B to Plasma), TFE3-deficient B cells may cause a defect of B cells to respond to signals from T cells |
| muEBP-C2 | 412+; 1294+ | MOUSE$IGH_10 | CATGTG | | 100 | Patch | Proteins Binding to Site C2 (muE3) in the Immunoglobulin Heavy-Chain |
| IRF | 748+ | V$IRF_Q6 | ttcccTTTCActtct | 1 | 0.975 | HQ | Expressed in spleen, thymus. mRNA induced by IFN-gamma, STAT-like element |
| NF-AT | 762-; 508+ | V$NFAT_Q6 | TttTTTCCtttc; tgttGGAAAcac | 1 | 0.992 | Immuo | Aactivated T cells |
| NF-Y | 893- | V$NFY_Q6 | TtaATTGGtta | 1 | 0.976 | HQ | Activator |
| AP-1 | 1296+; 1927+ | V$AP1_Q4; V$AP1_Q2 | TgTGACTcagc; gaTGACTgctt | 1 | 0.975 | Immuo/HQ | Interactive with c-Ets-1 and NF-Atp |
| Nkx2-5 | 1390-; 212- | V$NKX2501 | CACTTga | 1 | 1 | HQ | Lymph node stroma: TSL-1 [1] |
| YY1 | 1540+ | MOUSE$CR2_05 | CCTGTCTTC | | 100 | Patch | Ubiquitous repressor |
| LEF-1 | 1601- | V$LEF1_Q6 | ccCTTTGatt | 1 | 0.957 | Immuo/HQ | Ppotent activator in pre-B cells, T lymphocytes |

TABLE 3-continued

Sequence motifs in the LC-V promoter relevant to transcription

| Transcription factor | Position in p1612 | Binding site ID | Sequence recognized by TF | Core score | Matrix/patch | Sources/Search method | Annotation |
|---|---|---|---|---|---|---|---|
| yF-1/Ikaros | 1657+ | HS$LCK_02 | CCTCCCAAC | | 100 | Patch | Expressed in B (from Progentitor to Plasma) and T cell, lack of Ikarus (LyF-1) activity at the late stages of thymocyte maturation leads to uncontrolled lymphoproliferation |
| c-Ets-1 | 1840-; 1545- | V$ETS_1B;MOU SE$TIMP1_02 | gtgattacTTCCTgt; CAGGAAG | 1 | 0.964 | Immuo/Patch | Accelerated B cell development from pro B to Plasma |
| c-Ets-2 | 1842- | V$ETS2_B | gattacTTCCTgtc | 1 | 0.97 | Immuo/HQ | Mmitogenic and oncogenic activity |
| POU2F1a (Oct-1) | 1934- | V$OCT1_B | gcttTGCATa | 1 | 0.954 | HQ | DNA-binding is reduced by GR in a ligand-dependent manner |

Footnotes for Tables 2 and 3:
Positions in vectors correspond to the first nucleotide of the sequence shown; "+" indicates plus strand; "-" indicates minus strand.
Binding site ID is the transcription factor binding site identification assigned by TRANSFAC database.
Core score indicates core binding score calculated by TRANSFAC for the five most conserved, consecutive nucleotides used in a matrix.
Score is from 0 to 1, with 1 being the best score. For patch search the core score is 0.
Match/patch score indicates the similarity of a subsequence to a matrix of TRANSFAC. Score is from 0 to 1, with 1 being the best match.
If the score is 100, it was a Patch search.
Source/Search method indicates whether immuo-cell specific matrix model, high quality matrix model, and/or patch search method was used.

Summary of Vector Properties

The unique HC-C and LC-V promoters described here have been shown to be capable of driving high levels of gene expression. The HC-C and LC-C vectors allow convenient cloning into a final expression vector. The identification of sequence motifs that can determine transcriptional levels provides information to enhance gene transcription by customizing promoter and enhancer sequences and using host cells that express the best combination of transcription factors for these promoters. This could include using a host cell that has been modified to overexpress transcription factors that can enhance expression and/or a host cell that has been modified to underexpress transcription factors that may impede expression, among others. For example, host cells can be co-transfected with a gene encoding OBF-1 transcription factor to obtain higher OBF-1 levels, or using anti-sense, interfering RNA (e.g., siRNA or shRNA), or gene knockout approaches to reduce expression of TFs that may negatively regulate Ig gene transcription, e.g., NF-µNR.

The present invention also comprises methods of identifying the interaction between the sequences of promoter and enhancer regions and transcription factors in vectors/plasmids and cellular hosts, moderating the interaction by altering the sequences to effect transcription, translation, and gene expression levels, and determining the modifications and adjusting in order to control the levels. The sequence alteration may be by mutations to the sequences in the regions or by complete replacement of the regions compatible with the cell line used.

1. Although illustrated and described above with reference to certain specific embodiments, the present invention is nevertheless not intended to be limited to the details shown. Rather, the present invention is directed to an expression vector or plasmid having various sequences, apparatus, and kits disclosed herein and uses thereof, and various modifications may be made in the details within the scope and range of equivalents of the claims and without departing from the spirit of the invention.

What is claimed:

1. A mammalian expression vector comprising the nucleotide sequence of SEQ ID NO: 1, SEQ ID NO: 5, or SEQ ID NO: 6.

2. The vector of claim 1 further comprising a polynucleotide sequence encoding a variable region of an antibody.

3. The vector of claim 2 wherein the polynucleotide sequence encoding a variable region encodes a heavy or light chain of an antibody.

4. The vector of claim 1, further comprising any one of the group consisting of a 5' flanking sequence, an immunoglobulin promoter region, a cloning site, an intron enhancer region, a selectable marker, and an antibiotic resistance gene.

5. The vector of claim 4 wherein expression of the selectable marker confers resistance to at least one selected from mycophenolic acid (gpt gene), hygromycin, neomycin, Zeocin™, kanamycin, blasticidin, and G-418.

6. The vector of claim 4 wherein the antibiotic is selected from ampicillin, chloramphenicol, and kanamycin.

7. A host cell comprising the expression vector according to claim 1.

8. The host cell of claim 7, wherein the host cell is a mammalian host cell.

9. The host cell of claim 8 wherein the host cell is a murine myeloma host cell.

10. A kit comprising the vector of claim 1.

11. A method for producing at least one antibody, comprising translating a nucleic acid in the expression vector according to claim 2, under conditions in vitro, in vivo or in situ, wherein the antibody is expressed in detectable or recoverable amounts.

* * * * *

UNITED STATES PATENT AND TRADEMARK OFFICE
CERTIFICATE OF CORRECTION

PATENT NO.         : 8,663,980 B2                                     Page 1 of 1
APPLICATION NO. : 12/738453
DATED              : March 4, 2014
INVENTOR(S)        : Carton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 898 days.

Signed and Sealed this
Twenty-ninth Day of September, 2015

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 5173
<212> TYPE: DNA
<213> ORGANISM: Artificial Sequence
<220> FEATURE:
<223> OTHER INFORMATION: Vector suitable for mammalian cells

<400> SEQUENCE: 1
tctagagaag actttagagt agaatctgag gctcacctca cataccagca agggagtgac      60
```

```
cagttagtct taaggcacca ctgagcccaa gtcttagaca tcatggcttg ggtgtggacc      120
ttgctattcc tgatggcagc tgcccaaagt aagacatcag aaaaaaagag ttccaaggga      180
aattgaagca gttccatgaa tactcacctt cctgtgttct tttcacaggt atacaggcct      240
ctgtcccctg ctccactcct taaagagacc aggaagtttc tcccccaacg caagacagac      300
acaagcagac agaatctcag agaaaagagg tttattgggt ttcacagatg gtgcaggggg      360
tccctgtgga tgtctagcca agcagtggct ggcttttaga gcttcgtgct ttcttctaga      420
accccttggt cacccacatc taattctctc gccatctctc tcttagatgg gtcctgtctg      480
aggtgagaca cctttgtgtc tgggacctag ttgtcatctg acggctttct attttccccc      540
tctttctatt ctctataaat aaataactta acttttctct ccataaatag tcaaccttcc      600
cctgttccca gccacctctc ccatgtctgt ccctccttca tgtccaggtc tctgtccgac      660
ctagacccac aaaaaccctg ctctgtgcag gaacttctag gtaggcttga gtcgtcccct      720
gagcatctgg agtggccctg gggaagatgt agtcccctga agtgtctcag actcccgtga      780
gagctccagg ttattttagt ggggaaggct ggagactgtg gggatgtgac ccttgaaaca      840
acggtcagga tggaggcctg gaatccaatt cttgggtttc tttagaatct acagtgcaaa      900
ggctccaaag aatacactgc tggggctgaa gtgtagatgg gagatgccgt cggtgtgggt      960
ggacagctgt tctcccttac tgagcaggaa cacagccccc tggtacattg agcgcaccca     1020
cggtccttga agtcccggat acacagactt ctgcgcactg aggagaggca catggaaggg     1080
gtattgggag gaaaagagct ggacctcgtg tgccaggtag atgggagtgg gaatggccct     1140
gggggagcag ctttctccag agaaaaccac ctgggagtag acaaagtaga ggccactggt     1200
ggggatcagg agggagttgt tgctcaaaga gaagccatgt cggagaaagg cacgatccgt     1260
gcttgctctc cagagcagtg agttctgctt gctggggtac cttagtcacc gtctcctcag     1320
gtaagaatgg cctctccagg tctttatttt taacctttgt tatggagttt tctgagcatt     1380
gcagactaat cttggatatt tgccctgagg gagccggctg agagaagttg ggaaataaat     1440
ctgtctaggg atctcagagc ctttaggaca gattatctcc acatctttga aaaactaaga     1500
atctgtgtga tggtgttggt ggagtccctg gatgatggga tagggacttt ggaggctcat     1560
ttgagggaga tgctaaaaca atcctatggc tggagggata gttggggctg tagttggaga     1620
ttttcagttt ttagaatgaa gtattagctg caatacttca aggaccacct ctgtgacaac     1680
cattttatac agtatccagg catagggaca aaaagtggag tggggcactt tctttagatt     1740
tgtgaggaat gttccacact agattgttta aaacttcatt tgttggaagg agctgtctta     1800
gtgattgagt caagggagaa aggcatctag cctcggtctc aaaagggtag ttgctgtcta     1860
gaggatctga gctccagctt ttgttccctt tagtgttaat tgcgcgcttg gcgtaatcat     1920
ggtcatagct gtttcctgtg tgaaattgtt atccgctcac aattccacac aacatacgag     1980
ccggaagcat aaagtgtaaa gcctggggtg cctaatgagt gagctaactc acattaattg     2040
cgttgcgctc actgcccgct ttccagtcgg gaaacctgtc gtgccagctg cattaatgaa     2100
tcggccaacg cgcggggaga ggcggtttgc gtattgggcg ctcttccgct tcctcgctca     2160
ctgactcgct gcgctcggtc gttcggctgc ggcgagcggt atcagctcac tcaaaggcgg     2220
taatacggtt atccacagaa tcaggggata acgcaggaaa gaacatgtga gcaaaaggcc     2280
agcaaaaggc caggaaccgt aaaaaggccg cgttgctggc gttttccat aggctccgcc      2340 cccctgacga gcatcacaaa aatcgacgct caagtcagag gtggcgaaac ccgacaggac     2400
tataaagata ccaggcgttt cccctggaa gctccctcgt gcgctctcct gttccgaccc      2460
```

```
tgccgcttac cggatacctg tccgcctttc tcccttcggg aagcgtggcg ctttctcata    2520
gctcacgctg taggtatctc agttcggtgt aggtcgttcg ctccaagctg ggctgtgtgc    2580
acgaaccccc cgttcagccc gaccgctgcg ccttatccgg taactatcgt cttgagtcca    2640
acccggtaag acacgactta tcgccactgg cagcagccac tggtaacagg attagcagag    2700
cgaggtatgt aggcggtgct acagagttct tgaagtggtg gcctaactac ggctacacta    2760
gaaggacagt atttggtatc tgcgctctgc tgaagccagt taccttcgga aaaagagttg    2820
gtagctcttg atccggcaaa caaaccaccg ctggtagcgg tggtttttt tgtttgcaagc    2880 agcagattac gcgcagaaaa aaggatctca agaagatcc tttgatcttt tctacggggt    2940
ctgacgctca gtggaacgaa aactcacgtt aagggatttt ggtcatgaga ttatcaaaaa    3000
ggatcttcac ctagatcctt ttcgaccgaa taaatacctg tgacggaaga tcacttcgca    3060
gaataaataa atcctggtgt ccctgttgat accgggaagc cctgggccaa cttttggcga    3120
aaatgagacg ttgatcggca cgtaagaggt tccaactttc accataatga ataagatca    3180 ctaccgggcg tattttttga gttgtcgaga ttttcaggag ctaaggaagc taaaatggag    3240
aaaaaaatca ctggatatac caccgttgat atatcccaat ggcatcgtaa agaacatttt    3300
gaggcatttc agtcagttgc tcaatgtacc tataaccaga ccgttcagct ggatattacg    3360 gccttttaa agaccgtaaa gaaaaataag cacaagtttt atccggcctt tattcacatt    3420
cttgcccgcc tgatgaatgc tcatccggaa ttacgtatgg caatgaaaga cggtgagctg    3480
gtgatatggg atagtgttca cccttgttac accgttttcc atgagcaaac tgaaacgttt    3540
tcatcgctct ggagtgaata ccacgacgat ttccggcagt ttctacacat atattcgcaa    3600
gatgtggcgt gttacggtga aaacctggcc tatttcccta aagggtttat tgagaatatg    3660
tttttcgtct cagccaatcc ctgggtgagt ttcaccagtt ttgatttaaa cgtggccaat    3720
atggacaact tcttcgcccc gttttcacca tgggcaaata ttatacgcaa ggcgacaagg    3780
tgctgatgcc gctggcgatt caggttcatc atgccgtttg tgatggcttc catgtcggca    3840
gaatgcttaa tgaattacaa cagtactgcg atgagtggca gggcggggcg taattttttt    3900
aaggcagtta ttggtgccct taaacgcctg gttgctacgc ctgaataagt gataataagc    3960
ggatgaatgg cagaaattcg aaagcaaatt cgacccggtc gtcggttcag ggcagggtcg    4020
ttaaatagcc gcttatgtct attgctggtt taccggttta ttgactaccg gaagcagtgt    4080
gaccgtgtgc ttctcaaatg cctgaggcca gtttgctcag gctctccccg tggaggtaat    4140
aattgacgat atgatccttt ttttctgatc aaaagtgctc atcattggaa aacgttcttc    4200
ggggcgaaaa ctctcaagga tcttaccgct gttgagatcc agttcgatgt aacccactcg    4260
tgcacccaac tgatcttcag catcttttac tttcaccagc gtttctgggt gagcaaaaac    4320
aggaaggcaa aatgccgcaa aaagggaat aagggcgaca cggaaatgtt gaatactcat    4380
actcttcctt tttcaatatt attgaagcat ttatcaaggg ttattgtctc atgagcggat    4440
acatatttga atgtatttag aaaaataaac aaataggggt tccgcgcaca tttccccgaa    4500
aagtgccacc taaattgtaa gcgttaatat ttgttaaaa ttcgcgttaa attttgtta    4560 aatcagctca ttttttaacc aataggccga atcggcaaa atcccttata atcaaaaga    4620 atagaccgag atagggttga gtgttgttcc agtttggaac aagagtccac tattaaagaa    4680
cgtggactcc aacgtcaaag ggcgaaaaac cgtctatcag ggcgatggcc cactacgtga    4740
accatcaccc taatcaagtt ttttggggtc gaggtgccgt aaagcactaa atcggaaccc    4800
taaagggagc ccccgattta gagcttgacg gggaaagccg gcgaacgtgg cgagaaagga    4860
```

-continued

| | |
|---|---|
| agggaagaaa gcgaaaggag cgggcgctag ggcgctggca agtgtagcgg tcacgctgcg | 4920 |
| cgtaaccacc acacccgccg cgcttaatgc gccgctacag ggcgcgtccc attcgccatt | 4980 |
| caggctgcgc aactgttggg aagggcgatc ggtgcgggcc tcttcgctat tacgccagct | 5040 |
| ggcgaaaggg ggatgtgctg caaggcgatt aagttgggta acgccagggt tttcccagtc | 5100 |
| acgacgttgt aaaacgacgg ccagtgagcg cgcgtaatac gactcactat agggcgaatt | 5160 |
| gggtacactc gac | 5173 |

```
<210> SEQ ID NO 2
<211> LENGTH: 17246
<212> TYPE: DNA
<213> ORGANISM: Artificial Sequence
<220> FEATURE:
<223> OTHER INFORMATION: Vector suitable for mammalian cells
<220> FEATURE:
<221> NAME/KEY: intron
<222> LOCATION: (4636)
<223> OTHER INFORMATION: Wherein n can be a, c, t or g
<220> FEATURE:
<221> NAME/KEY: unsure
<222> LOCATION: (10992)
<223> OTHER INFORMATION: Wherein n can be a, c, t or g
<220> FEATURE:
<221> NAME/KEY: unsure
<222> LOCATION: (11718)
<223> OTHER INFORMATION: Wherein n can be a, c, t or g
<220> FEATURE:
<221> NAME/KEY: unsure
<222> LOCATION: (11835)
<223> OTHER INFORMATION: Wherein n can be a, c, t or g
<220> FEATURE:
<221> NAME/KEY: unsure
<222> LOCATION: (12076)
<223> OTHER INFORMATION: Wherein n can be a, c, t or g
<220> FEATURE:
<221> NAME/KEY: unsure
<222> LOCATION: (12100)
<223> OTHER INFORMATION: Wherein n can be a, c, t or g

<400> SEQUENCE: 2
```

| | |
|---|---|
| gaattcacag ccactgcctt gggatcagtc tgtgccatta ttgttaggta gacatctctt | 60 |
| tagtgcacca tttgattata catacacaga cataccgaca aacacacaga aacacacaca | 120 |
| catataatat aataaataca aaataatata ataatatata tgtatatgtg tatatgaatg | 180 |
| tgtatgtaat gttgttgggg tctctcacct gctcaccaca ggatgccaca agtttgacca | 240 |
| agcttacctc aagctgtagc caggtgggtg ttgagccata aacagcact gggaccccac | 300 |
| ccaggcctgg aaaatcacag tctgaggctc aggacagcca atgctggctc gggggtcgcc | 360 |
| agacctaaaa aaggcaaagc catttgcctc tcagattctt gggcatcgag aggtcactgg | 420 |
| aagacatgga agagatgagg atatatgcat atacaattat tcacttttc acacattgct | 480 |
| tagtgaatat gaagcaatct tcttcattgc ctctaacgat ttcaggactg acatcaattc | 540 |
| tattacatat tataatacca aaacttattt gtcccttatt tccataggct ggataaacta | 600 |
| ccaacaaaag agtacatatg gtgggattca tggctctagc tgcataggta gcagaggatg | 660 |
| gcctagtcag tcatcaatgg gaggagaggt acttggttct atgaagattc tatacccag | 720 |
| tatagggaa tgacagggcc aggaagcaag agagggtgtg ttggtgagca ggggaagaag | 780 |
| gaggaggag gggaattttg gagaggaaac caggaaaggg cacaacagtt aaaatgtaaa | 840 |
| taaagtaaat atttaataaa aaataaataa aaagaactca agaatttaga ctccaaaaga | 900 |
| caaaataacc aaattaaaaa gtggagtaca gagctaatca gagtaatctc aacaaaaata | 960 |
| tctgtaatgg ccaagaagca cttaaagaaa tgtttgaaat ccccttaatca ccagtgaaat | 1020 |

```
gcaaatccaa tcaaccctca gattccacct tacactaatc agaaggtcta agttaaaaaa    1080
aaaaaaaaaa aaaaaaaact caagtgacag catattccta taaggatgtg aagcaaggca    1140 accagtctتt catagttagt gaaaataccc actggtacga ccactcaaaa tcaacctggt    1200
ggttcatcag aaaattggaa atagttctat ttgaaaactc agctatacca ctccacaata    1260
tcacaagaac ccgtatttca ctatgtccat aggggacttc ttcataatag ccagaaactg    1320
gaaacaacct aaatctatct cagttgaaga ctgggcagag aaaatgtatt tccttcatgc    1380
tgtagagtaa tcctcaccta ttaaagagta ggacattatg tattttgctg gcaaatgatg    1440
gtactagaaa atctatcctg attgaggtaa cccaaaccca aaagaaagtg aatggtatgt    1500
cgtcaatgaa acatggatat cagccaaaaa gcatgcctgc cacacaacat caatttctgg    1560
caaaggctac acttaactat ttctagtaga acagctcttt ggtttgccaa aaagaatcac    1620
ctatagtagc atctacgcac aaaaaggaga aaaaaatcac aaagaaatga tttagaagca    1680
taataaaaat tatcagaaaa ttatgagttt tgcgattgat ttcatctttc tccaagttga    1740
aatcatagag tggctttaac acagtgacaa ggaatgtgca tgatgcaatt atggtgctct    1800
gcctaaaatg gttggagcct tgtcatgcta caaagaatct gtcatacagc agggggtgcc    1860
aaatttctat attttttaa atatcattga gcaggtgcac agaagagcag aaagcacttt     1920
ctatcaggct ggccttcctc ttccttt cca gtatgaagca caaactgcca atgaaactag    1980
caattgttaa attcctttt caaacagtat ttgtgctatc agaacatagt gcattcaaaa     2040
gtctagcctg agagcacaac ccagttttat tcattcctcc tactaccttt ctcattccca    2100
ctgtttctgt tctccctccc attttaattg tctatctagt ccaaactaag cacactatgc    2160
agtccacatt aaacaacacg ttttcacttt aagtcaaata caagacacct ttaatatcag    2220
ccctcgtcca taatcgtgct tctagtgact taatgtacat gtcacactgt actgttgggt    2280
tttgtgtctc atcatgaaca gtgttgggaa agtattaaat agagagtaag cagaattaga    2340
ttcctctaat gatgcacacc cacacgaaga gcagaaataa tattaaaaat agaaaagag    2400 ttttacatga gatttcaaat acccgtgact gagctgcagt ttcttcaagt tacagcatcg    2460
aggttgtcag ttacactatt acaggaaaca tatgcagagt ttttttttta gtatattagt    2520
tttcacatat gtggaattac tattaaacta ttctttcttt tcaaatgctt accattgtaa    2580
atgagtttgg actttgtgta ggtgagtgca catgactctg gatgcctaag aggactgaag    2640
aagttggagt tataggtagt tttattctac ctgactgttc agtgctaaaa atacaactga    2700
ggtcctttga acttcttaat tgatatatct catgagatcc ctaaactatt tttattatca    2760
aacgtttcac cattttcact gtaatgattt ttatgtttta tattaatgta actatatgac    2820
acttcccaaa actccccatc ttcacaattg aactgtttca aagttttacc ttgacttatg    2880
ggaaatgaaa acccacattt tataatttta aaatgaaatg tttatttttct atttctgcaa    2940 atttcacaag gaaagattag tcactggtgt gggagagcag aggaccataa gagttcagga    3000
atagaatcca ttataattct ggagtcaagg aagtactgat gccaaggttt cattataaga    3060
gcaatatcca ctggaaagga taaagtcact acatctgagc acagagcagg acagctacct    3120
aatgagtggt cactaatggg ccactgttac actgttatat gtataaggct caggaatgag    3180
cactgaggct gtgaggtgta tgggtgagga catcaggatg taaacccagc tcaggtagag    3240
gactcagagg acagcacaat cagcatgaac taataaacat cagataagat aaggctcaag    3300
ctctagctat atagggtcag ggatcttgt aaatctgatt gtgtatccag tctagttcaa     3360
tgtgtcttag gaagcccagt catatgcaaa tctagagagg tctggtggag cctgcaaaag    3420
```

```
tccagctttc aaaggaacac agaagtatgt gtatggaata ttagaagatg ttgcttttac   3480
tcttaagttg gttcctagga aaaatagtta aatactgtga ctttaaaatg tgagagggtt   3540
ttcaagtact cattttttta aatgtccaaa attttttgtca atcaatttga ggtcttgttt   3600
gtgtagaact gacattactt aaagtttaac cgaggaatgg gagtgaggct ctctcatacc   3660
ctattcagaa ctgactttta acaataataa attaagttta aaatattttt aaatgaattg   3720
agcaatgttg agttgagtca agatggccga tcagaaccgg aacacctgca gcagctggca   3780
ggaagcaggt catgtggcaa ggctatttgg ggaagggaaa ataaaaccac taggtaaact   3840
tgtagctgtg gtttgaagaa gtggttttga aacactctgt ccagcccac caaaccgaaa    3900 gtccaggctg agcaaaacac cacctgggta atttgcattt ctaaaataag ttgaggattc   3960
agccgaaact ggagaggtcc tcttttaact tattgagttc aacctttaaa ttttagcttg    4020
agtagttcta gtttccccaa acttaagttt atcgacttct aaaatgtatt tagaattcat   4080
tttcaaaatt aggttatgta agaaattgaa ggactttagt gtctttaatt tctaatatat   4140
ttagaaaact tcttaaaatt actctattat tcttccctct gattattggt ctccattcaa   4200
ttcttttcca atacccgaag catttacagt gactttgttc atgatctttt ttagttgttt   4260
gttttgcctt actattaaga ctttgacatt ctggtcaaaa cggcttcaca aatctttttc   4320
aagaccactt tctgagtatt cattttagga gaaatacttt ttttttaaat gaatgcaatt   4380
atctagctag acttatttcg gttgaacatg ctggttggtg gttgagagga cactcagtca   4440
gtcagtggcg tgaagggctt ctaagccagt ccacatgctc tgtgtgaact ccctctggcc   4500
ctgcttattg ttgaatgggc caaaggtctg agaccaggct gctgctgggt aggcctggac   4560
tttggtctcc cacccagacc tgggaatgta tggtttggct tctgccaccc atccacctgg   4620
ctgctcatgg accagnctcg gtggctttga aggaacaatt ccacacaaag actctggacc   4680
tctccgaaac caggcaccgc aaatggtaag ccagaacgcg gctgtggctg ctgctcttaa   4740
agcttgtaaa ctgtttctgc ttaagaggga ctgagtcttc agtcattgct ttagggggag   4800
aaagagacat ttgtgtgtct tttgagtacc gttgtctggg tcactcacat ttaacttttcc   4860 ttgaaaaact agtaaaagaa aaatgttgcc tgttaaccaa taatcataga gctcatggta   4920
ttttgaggaa atcttagaaa acgtgtatac aattgtctgg aattatttca gttaagtgta   4980
ttagttgagg tactgatgct gtctctactt cagttataca tgtgggtttg aattttgaat   5040
ctattctggc tcttcttaag cagaaaattt agataaaatg gatacctcag tggttttttaa   5100 tggtgggttt aatatagaag gaatttaaat tggaagctaa tttagaatca gtaaggaggg   5160
acccaggcta agaaggcaat cctgggattc tggaagaaaa gatgttttta gtttttatag   5220
aaaacactac tacattcttg atctacaact caatgtggtt taatgaattt gaagttgcca   5280
gtaaatgtac ttcctggttg ttaaagaatg gtatcaaagg acagtgctta gatccaaggt   5340
gagtgtgaga ggacaggggc tggggtatgg atacgcagaa ggaaggccac agctgtacag   5400
aattgagaaa gaatagagac ctgcagttga ggccagcagg tcggctggac taactctcgt   5460
aatgacccag acagagaagg ccagactcat aaagctggtc gatcgacccc aggcctgacc   5520
ttggctttgg ggcagggagg gggctaaggt gaggcaggtg gcgccagcag gtgcacaccc   5580
aatgcccatg agcccagaca ctggacgctg aacctcgcgg acagttaaga acccaggggc   5640
ctctgcgcct gggcccagct ctgtcccaca ccgcggtcac atggcaccac ctctcttgca   5700
gcctccacca agggcccatc ggtcttcccc ctggcaccct cctccaagag cacctctggg   5760
ggcacagcgg ccctgggctg cctggtcaag gactacttcc ccgaaccggt gacggtgtcg   5820
```

-continued

```
tggaactcag gcgccctgac cagcggcgtg cacaccttcc cggctgtcct acagtcctca    5880
ggactctact ccctcagcag cgtggtgacc gtgccctcca gcagcttggg cacccagacc    5940
tacatctgca acgtgaatca caagcccagc aacaccaagg tggacaagaa agttggtgag    6000
aggccagcac agggagggag ggtgtctgct ggaagcaggc tcagcgctcc tgcctggacg    6060
catcccggct atgcagcccc agtccagggc agcaaggcag gccccgtctg cctcttcacc    6120
cggagcctct gcccgcccca ctcatgctca gggagagggt cttctggctt tttcccaggc    6180
tctgggcagg cacaggctag gtgccccgtaa cccaggccct gcacacaaag ggcaggtgc    6240
```

```
tgggctcaga cctgccaaga gccatatccg ggaggaccct gccctgacc taagcccacc     6300 ccaaaggcca aactctccac tccctcagct cggacaccgt ctctcctccc agattccagt    6360
aactcccaat cttctctctg cagagcccaa atcttgtgac aaaactcaca catgcccacc    6420
gtgcccaggt aagccagccc aggcctcgcc ctccagctca aggcgggaca ggtgccctag    6480
agtagcctgc atccagggac aggcccccagc cgggtgctga cacgtccacc tccatctctt    6540
cctcagcacc tgaactcctg gggggaccgt cagtcttcct cttcccccca aacccaagg     6600 acaccctcat gatctcccgg accctgagg tcacatgcgt ggtggtggac gtgagccacg     6660
aagaccctga ggtcaagttc aactggtacg tggacggcgt ggaggtgcat aatgccaaga    6720
caaagccgcg ggaggagcag tacaacagca cgtaccgggt ggtcagcgtc ctcaccgtcc    6780
tgcaccagga ctggctgaat ggcaaggagt acaagtgcaa ggtctccaac aaagccctcc    6840
cagcccccat cgagaaaacc atctccaaag ccaaaggtgg gacccgtggg gtgcgagggc    6900
cacatggaca gaggccggct cggcccaccc tctgccctga gagtgaccgc tgtaccaacc    6960
tctgtcctac agggcagccc cgagaaccac aggtgtacac cctgccccca tcccgggatg    7020
agctgaccaa gaaccaggtc agcctgacct gcctggtcaa aggcttctat cccagcgaca    7080
tcgccgtgga gtgggagagc aatgggcagc cggagaacaa ctacaagacc acgcctcccg    7140
tgctggactc cgacggctcc ttcttcctct acagcaagct caccgtggac aagagcaggt    7200
ggcagcaggg gaacgtcttc tcatgctccg tgatgcatga ggctctgcac aaccactaca    7260
cgcagaagag cctctccctg tctccgggta aatgagtgcg acggccggca agccccgctc    7320
cccgggctct cgcggtcgca cgaggatgct tggcacgtac ccctgtaca tacttcccgg     7380 gcgcccagca tggaaataaa gcaccagcg ctgccctggg cccctgcgag actgtgatgg     7440
ttctttccac gggtcaggcc gagtctgagg cctgagtggc atgagggagg cagagcgggt    7500
cccactgtcc ccacactggc ccaggctgtg caggtgtgcc tgggccgcct agggtggggc    7560
tcagcagggg gctccctcgg caggtggggg atttgccagc gtggccctcc ctccagcagc    7620
acctgccctg ggcctccacg ggaagcccta ggagcccctg ggacagaca cacagcccct     7680 gcctctgtag gagactgtcc tgttctgtga gcgccctgtc ctccgacctc catgcccact    7740
cgggggactg cctagtccat gtgcgtaggg acaggccctc cctcacccat ctaccccac     7800 ggcactaacc cctggctgcc ctgcccagcc tcgcacccgc atgcggacac aaccgactcc    7860
ggggacatgc actctcgggc cctgtggagg actggtgca gatgcccaca cacacactca     7920
gcccagaccc gttcaacaaa ccccgcactg aggttggccc gcacacggcc accacacaca    7980
cacgtgcacg cctcacacac ggagcctcac cccgggcgaa ctgcacagca cccagaccag    8040
agcggaatcc tcgcacacgt gaacactcct cggacacagg ccccacgag cccacgcgg      8100 cacctcaagg cccacgagcc tctcggcagc ttctccacat gctgacctgc tcagacaaac    8160
ccagccctcc tctcacaagg gtgccctgc agccgccaca cacacacagg ggatcacaca     8220
```

```
ccacgttcac gctccctggc cctggccact tcctgcagct ggggtaatag tgtgggcttc    8280
accatcctcc tgccctctcc gtcagggagg gacacgggag acggggagcg ggtcctgctg    8340
agggccaggt cgctatctag ggccgggtgt ctggctgagc ccggggccaa agctggtgcc    8400
cagggggca gctgtgggga gctgacctca ggacattgtt ggcccatccc ggccggccct    8460
acatctgggc ccgcacagag ggaatcaccc cagaggccc aagccagggg acacagcact    8520
ggaccacccc cttactgtcc agagctgcaa ctggaggaga gctgtsgags saggacgggg    8580
agctggacgg gctgtggacg accatcacca tcttcatcac actcttcctg ttaagcgtgt    8640
gctacagtgc caccgtcacc ttcttcaagg tcggccgcac gttgtcccca gctgtccttg    8700
acattgtccc ccatgctgtc acaaactgtc tctgacactg tcccacaggc tgtccccacc    8760
tgtccctgac gctgtccccc atgctctcac aaactgtccc tgacattgtc cccaatgctg    8820
ccccacctg tccaacagtg tcccccaggc tctccccaca tgtccccgac actgtccccc    8880
atgctgtccc catctgtccc caacactgtc ccccaccctg tccccctttg tccccaacac    8940
tgtcccccac agtttccacc tgtccctgac actcccccat gctttcccca cctgtccctg    9000
acaccatccc ccactctgtc ccctatagtt cctggccctg tccccacgc tgtccctac    9060
agtacctggc actgtccccc atgctgtccc ctcctgtatg aaaccctgtc ccacatgctg    9120
tccccacctg tccgtgacaa tatccccac actgtcccca cctgtcccg acactctcct    9180
ccacgttgtt cttacctaaa cccgacactt cctccatgc tgtccccacc catctccgac    9240
actgtacccc acgttgtccc cacctgtcct caacactgtc cccatgctg tccccacctg    9300
tccctgacac tgtccccat gctgtcccca cctgtccgg acactgttct ccacgctctc    9360
ccctcctgtc cccgacactg tccccacac tgtccccacc tgtccccaac actatcctcc    9420
atgctgtccc ctcctgtccc cacctgtccc ctacactgtc cccatgctg tccccaccag    9480
tccccaaaac tttcctccac actgtcccca cctgtcccca acactgtccc ccacgctatc    9540
ccccctgtcc ccgacaatgt ccccactgtt tcctcctgtt ccctcctatc cctgacactg    9600
tccgccatgc tgtccccacc tgtccctgac actgtctccc actctgtccc ctataatccc    9660
tgacactgtc ccccacgccg tccctcccg tatgcaccac tgtcccccaa gctgtcccca    9720
ccagtccccca acactgtccc ccatgctgtc cccacctgtc cccaacactc tcctccatgt    9780
ccccacctgt ccctgatatt gtccccatg cagtccccac ctgtccccga tgctgtcccc    9840
cgggctgtac ctaccagtcc aacactgtcc cccacactct ccccacctgt ccctgatact    9900
gtccccatg ctgtccccac ctgtcccgga cactgttctc cacgctctcc cctcctgtcc    9960
ctgacactgt ccccacact gtccccacct gtccccaaca ctatcctcca tcctgtccca    10020
acctgtctcc tacactgtcc cccatgctgt ccccaccagt ccccaacact gtcctccatg    10080
ctgtcccca tgtccccaac actgtccccc atgctatctc cctgtccct gacaatgtcc    10140
ccactgtttc ctgtcccctc ctatccctga ctgtccgc catgctgtcc ccacctgtcc    10200
cccacatggt ctccaccggt ccctgacact gtcccact ctgtccccta taatccctga    10260
cactgtcccc cacaccgtcc cctcctgtat gcaccactgt ccccatgct gtccccacct    10320
gtccctgatg ctgtcctcca cacagtccc acctctccct gacactgtcc ccatctctcc    10380
ccaacactct cctccatgct gtcctcaact gtccccaaca ctcttccaca ctctgtctcc    10440
acctgtccct gacactgtcc ccacactgt cctcacctgt gtctgacact gtccccacg    10500
ctgtccccac ctgtccctga cgctgtcttc tgtgctgtcc acatgctgtt ggtgccctgg    10560
ctctgctctc tatcaccaag cctcagagca ggcagtggtg aggccatggc acctgggtgg    10620
```

```
catgaggggc cggatgggcc tcaggggcag ggctgtggcc tgcgtggact gacgggtggg   10680
tgggccttgg gggcagagag gtggcctcag tgccctgagg ggtgggtggg gctcggggc    10740 agggctgtgg cctcgctcac ccctgtgctg tgccttgcct acaggtgaag tggatcttct   10800
cctcggtggt ggacctgaag cagaccatca tccccgacta caggaacatg atcggacagg   10860
gggcctaggg caccctctgc ggggtgtcag ggccgcccag accccacaca ccagcatggg   10920
ccatgctcag ccaccaccca ggccacacct gccccgacct caccgccctc aacccatggc   10980
tctctggcct cngagttgcc tctgacctga cacacctgac acacctgaca cggcccccct   11040
tccagacctg tgcatagcag gtctaccccca gacctccgct gcttggtgca tgcagggcac   11100
tgggggcagg tgtcctcagc aggacatcct tccctcgacc acaaggtgct cacacaaaag   11160
gaggcagtga ccggtatcca ggcccccacc caggcaggag ctgccctgga gccaaccccg   11220
tccacgccag cctcctgaac acaggcgtgg tttccagatg gtgagtggga gcatcagccg   11280
gccaaggtag ggaagccaca gcaccatcag gcctgttggg gaggcttccg agagctgcga   11340
aggctcactc agacggcctt ctcccagcc cgcagccagc cagcctccat tccggcactc    11400
ccgtaactcc tacatgagaa tgagttgttc tgatttcaag caaagaacgc tgctctctgg   11460
ctcctgggaa cagtctcggt gccagcacca cccttggct gcctggccca cactgctgga    11520
ttctcgggtg gaactggacc gcagggacag ccagccccag agtccgctct ggggagagaa   11580
ggccaggccc agacactgcc acctcccacc cactccagtc caccgagatc actcagagaa   11640
gagcctggcc atgtggccgc tgcaggagcc ccacagtgca aggtgagga tagcccaagg     11700 aagggctggg catctgcnac aggcctccca gagaaggctg gtgaccaggt cccaggcggc   11760
aagactcagc cttggtgggg cctgaggaca gaggaggccc aggagcatcg gggagagagg   11820
tggagggaca ccggngagag ccaggagcgt ggacacagcc agaactcatc acagaggctg   11880
gcgtccagtc ccgggtcacg tgcagcagga acaagcagcc actctggggc accaggtgga   11940
gaggcaagac gacaaagagg gtgcccgtgt tcttgcgaaa gcggggctgc tggccacgag   12000
tgctggacag aggcccccag cctctgctgc ccccatcacg ccgttccgtg actgtcacgc   12060
agaatccgca gacagnaagg gagactcgag cgggagtcgn gccagcgcct gcctcggccg   12120
tcagggagga ctcccgggct cactcgaagg aggtgccacc atttcagctt tggtagcttt   12180
tcttcttctt ttaaattttc taaagctcat taattgtctt tgatgtttct tttgtgatga   12240
caataaaata tccttttttaa gtcttgtact tcgtgatggg agccgccttc ctgtgtccac   12300
gcgcctcctg ccccggtggg aagcacagtc aggaggaggc tggtccagct gcacctcggg   12360
ggctccctcg atacgccccc cgcctcctgc agccacacgc attgcccgag cgaccctccc   12420
tggcccctgt cgctacatgg acccctgggc ttctcctctt ttctacatgg atgcagtttc   12480
tcctcctgct gggcacggtg ctgcctgccc tggtcactct gcgggggaca ggcctccagg   12540
gaaagctggg tcgaggctgg gagctggctc agactggcca gcagagccca ccaggagggg   12600
ccttccagaa cccaaccatg gtccgaagcg agaggtgggt gtcagatctg tgtgagtcag   12660
ctcaggacca cagcggggcg gctcccacgg caacatggat ccgtcgacgc ggccgcgatc   12720
cagacatgat aagatacatt gatgagtttg gacaaaccac aactagaatg cagtgaaaaa   12780
aatgctttat ttgtgaaatt tgtgatgcta ttgcttattt tgtaaccatt ataagctgca   12840
ataaacaagt taacaacaac aattgcattc attttatgtt tcaggttcag ggggaggtgt   12900
gggaggtttt ttaaagcaag taaaacctct acaaatgtgg tatggctgat tatgatctct   12960
agtcaaggca ctatacatca aatattcctt attaacccct ttacaaatta aaaagctaaa   13020
```

```
ggtacacaat ttttgagcat agttattaat agcagacact ctatgcctgt gtggagtaag    13080
aaaaaacagt atgttatgat tataactgtt atgcctactt ataaaggtta cagaatattt    13140
ttccataatt ttcttgtata gcagtgcagc ttttcctttt gtggtgtaaa tagcaaagca    13200
agcaagagtt ctattactaa acacagcatg actcaaaaaa cttagcaatt ctgaaggaaa    13260
gtccttgggg tcttctacct ttctcttctt ttttggagga gtagaatgtt gagagtcagc    13320
agtagcctca tcatcactag atggcatttc ttctgagcaa acaggtttt cctcattaaa    13380 ggcattccac cactgctccc attcatcagt tccataggtt ggaatctaaa atacacaaac    13440
aattagaatc agtagtttaa cacattatac acttaaaaat tttatattta ccttagagct    13500
ttaaatctct gtaggtagtt tgtccaatta tgtcacacca cagaagtaag gttccttcac    13560
aaagatccgg ggcccactca taaatccagt tgccgccacg gtagccaatc accgtatcgt    13620
ataaatcatc gtcggtacgt tcggcatcgc tcatcacaat acgtgcctgg acgtcgagga    13680
tttcgcgtgg gtcaatgccg cgccagatcc acatcagacg gttaatcatg cgataccagt    13740
gagggatggt tttaccatca agggccgact gcacaggcgg ttgtgcgccg tgattaaagc    13800
ggcggactag cgtcgaggtt tcaggatgtt taaagcgggg tttgaacagg gtttcgctca    13860
ggtttgcctg tgtcatggat gcagcctcca gaatacttac tggaaactat tgtaacccgc    13920
ctgaagttaa aaagaacaac gcccggcagt gccaggcgtt gaaaagatta gcgaccggag    13980
attggcggga cgaatacgac gcccatatcc cacggctgtt caatccaggt atcttgcggg    14040
atatcaacaa catagtcatc aaccagcgga cgaccagccg gttttgcgaa gatggtgaca    14100
aagtgcgctt ttggatacat ttcacgaatc gcaaccgcag taccaccggt atccaccagg    14160
tcatcaataa cgatgaagcc ttcgccatcg ccttctgcgc gtttcagcac tttaagctcg    14220
cgctggttgt cgtgatcgta gctggaaata caaacggtat cgacatgacg aatacccagt    14280
tcacgcgcca gtaacgcacc cggtaccaga ccgccacggc ttacggcaat aatgcctttc    14340
cattgttcag aaggcatcag tcggcttgcg agtttacgtg catggatctg caacatgtcc    14400
caggtgacga tgtatttttc gctcatgtga agtgtcccag cctgtttatc tacggcttaa    14460
aaagtgttcg aggggaaaat aggttgcgcg agattataga gatctggcgc actaaaaacc    14520
agtatttcac atgagtccgc gtctttttac gcactgcctc tccctgacgc gggataaagt    14580
ggtattctca acatatctc gcaagcctgt cttgtgtcca agctagctttt ttgcaaaagc    14640 ctaggcctcc aaaaaagcct cctcactact tctggaatag ctcagaggcc gaggcggcct    14700
cggcctctgc ataaataaaa aaaattagtc agccatgggg cggagaatgg gcggaactgg    14760
gcggagttag gggcgggatg ggcggagtta ggggcgggac tatggttgct gactaattga    14820
gatgcatgct ttgcatactt ctgcctgctg gggagcctgg ttgctgacta attgagatgc    14880
atgctttgca tacttctgcc tgctggggag cctggggact ttccacaccc taactgacac    14940
acattccaca gctgcctcgc gcgtttcggt gatgacggtg aaaacctctg acacatgcag    15000
ctcccggaga cggtcacagc ttgtctgtaa gcggatgccg ggagcagaca agcccgtcag    15060
ggcgcgtcag cgggtgttgg cgggtgtcgg ggcgcagcca tgacccagtc acgtagcgat    15120
agcggagtgt atactggctt aactatgcgg catcagagca gattgtactg agagtgcacc    15180
atatgcggtg tgaaataccg cacagatgcg taaggagaaa ataccgcatc aggcgctctt    15240
ccgcttcctc gctcactgac tcgctgcgct cggtcgttcg gctgcggcga gcggtatcag    15300
ctcactcaaa ggcggtaata cggttatcca cagaatcagg ggataacgca ggaaagaaca    15360
tgtgagcaaa aggccagcaa aaggccagga accgtaaaaa ggccgcgttg ctggcgtttt    15420
```

```
tccataggct ccgccccct gacgagcatc acaaaaatcg acgctcaagt cagaggtggc    15480
gaaacccgac aggactataa agataccagg cgtttccccc tggaagctcc ctcgtgcgct    15540
ctcctgttcc gaccctgccg cttaccggat acctgtccgc ctttctccct cgggaagcg     15600 tggcgctttc tcatagctca cgctgtaggt atctcagttc ggtgtaggtc gttcgctcca    15660
agctgggctg tgtgcacgaa ccccccgttc agcccgaccg ctgcgcctta ccggtaact     15720 atcgtcttga gtccaacccg gtaagacacg acttatcgcc actggcagca gccactggta    15780
acaggattag cagagcgagg tatgtaggcg gtgctacaga gttcttgaag tggtggccta    15840
actacggcta cactagaagg acagtatttg gtatctgcgc tctgctgaag ccagttacct    15900
tcggaaaaag agttggtagc tcttgatccg gcaaacaaac caccgctggt agcggtggtt    15960
tttttgtttg caagcagcag attacgcgca gaaaaaaagg atctcaagaa gatcctttga    16020
tcttttctac ggggtctgac gctcagtgga acgaaaactc acgttaaggg attttggtca    16080
tgagattatc aaaaaggatc ttcacctaga tccttttaaa ttaaaaatga gttttaaat     16140 caatctaaag tatatatgag taaacttggt ctgacagtta ccaatgctta atcagtgagg    16200
cacctatctc agcgatctgt ctatttcgtt catccatagt tgcctgactc cccgtcgtgt    16260
agataactac gatacgggag ggcttaccat ctggccccag tgctgcaatg ataccgcgag    16320
acccacgctc accggctcca gatttatcag caataaacca gccagccgga agggccgagc    16380
gcagaagtgg tcctgcaact ttatccgcct ccatccagtc tattaattgt tgccgggaag    16440
ctagagtaag tagttcgcca gttaatagtt tgcgcaacgt tgttgccatt gctgcaggca    16500
tcgtggtgtc acgctcgtcg tttggtatgg cttcattcag ctccggttcc caacgatcaa    16560
ggcgagttac atgatccccc atgttgtgca aaaaagcggt tagctccttc ggtcctccga    16620
tcgttgtcag aagtaagttg gccgcagtgt tatcactcat ggttatggca gcactgcata    16680
attctcttac tgtcatgcca tccgtaagat gcttttctgt gactggtgag tactcaacca    16740
agtcattctg agaatagtgt atgcggcgac cgagttgctc ttgcccggcg tcaacacggg    16800
ataataccgc gccacatagc agaactttaa aagtgctcat cattggaaaa cgttcttcgg    16860
ggcgaaaact ctcaaggatc ttaccgctgt tgagatccag ttcgatgtaa cccactcgtg    16920
cacccaactg atcttcagca tcttttactt tcaccagcgt ttctgggtga gcaaaaacag    16980
gaaggcaaaa tgccgcaaaa aagggaataa gggcgacacg gaaatgttga atactcatac    17040
tcttcctttt tcaatattat tgaagcattt atcagggtta ttgtctcatg agcggataca    17100
tatttgaatg tatttagaaa aataaacaaa taggggttcc gcgcacattt ccccgaaaag    17160
tgccacctga cgtctaagaa accattatta tcatgacatt aacctataaa aataggcgta    17220
tcacgaggcc ctttcgtctt caagaa                                          17246
```

<210> SEQ ID NO 3
<211> LENGTH: 6701
<212> TYPE: DNA
<213> ORGANISM: Artificial Sequence
<220> FEATURE:
<223> OTHER INFORMATION: Vector suitable for mammalian cells
<220> FEATURE:
<221> NAME/KEY: intron
<222> LOCATION: (2648)
<223> OTHER INFORMATION: Wherein n can be a, c, t or g
<220> FEATURE:
<221> NAME/KEY: intron
<222> LOCATION: (2656)
<223> OTHER INFORMATION: Wherein n can be a, c, t or g
<220> FEATURE:
<221> NAME/KEY: intron

```
<222> LOCATION: (2927)
<223> OTHER INFORMATION: Wherein n can be a, c, t or g
<220> FEATURE:
<221> NAME/KEY: intron
<222> LOCATION: (2980)
<223> OTHER INFORMATION: Wherein n can be a, c, t or g
<220> FEATURE:
<221> NAME/KEY: intron
<222> LOCATION: (2985)
<223> OTHER INFORMATION: Wherein n can be a, c, t or g
<220> FEATURE:
<221> NAME/KEY: intron
<222> LOCATION: (3057)
<223> OTHER INFORMATION: Wherein n can be a, c, t or g
<220> FEATURE:
<221> NAME/KEY: intron
<222> LOCATION: (3072)
<223> OTHER INFORMATION: Wherein n can be a, c, t or g
<220> FEATURE:
<221> NAME/KEY: intron
<222> LOCATION: (3073)
<223> OTHER INFORMATION: Wherein n can be a, c, t or g
<220> FEATURE:
<221> NAME/KEY: intron
<222> LOCATION: (3074)
<223> OTHER INFORMATION: Wherein n can be a, c, t or g
<220> FEATURE:
<221> NAME/KEY: intron
<222> LOCATION: (3075)
<223> OTHER INFORMATION: Wherein n can be a, c, t or g
<220> FEATURE:
<221> NAME/KEY: intron
<222> LOCATION: (3076)
<223> OTHER INFORMATION: Wherein n can be a, c, t or g
<220> FEATURE:
<221> NAME/KEY: intron
<222> LOCATION: (3077)
<223> OTHER INFORMATION: Wherein n can be a, c, t or g
<220> FEATURE:
<221> NAME/KEY: intron
<222> LOCATION: (3146)
<223> OTHER INFORMATION: Wherein n can be a, c, t or g
<220> FEATURE:
<221> NAME/KEY: intron
<222> LOCATION: (3151)
<223> OTHER INFORMATION: Wherein n can be a, c, t or g
<220> FEATURE:
<221> NAME/KEY: intron
<222> LOCATION: (3171)
<223> OTHER INFORMATION: Wherein n can be a, c, t or g
<220> FEATURE:
<221> NAME/KEY: intron
<222> LOCATION: (3172)
<223> OTHER INFORMATION: Wherein n can be a, c, t or g

<400> SEQUENCE: 3
gagcttctcg agagaattca atttcactgt caaaagtcat catatggtct ccattactgg      60
cagcctactt gatttgagac acttgtttac aacaaagcca tgcataggta atcctctctg     120
gaggcaccct aagcccctgc accaactgta tttcagtctt gcttgcacag tcaaatcctg     180
tcccaatagc agctaggctg ctcaccacgg ctctgttgtc cttthcacttg agtgtataaa     240 agggagtaac aagggaaga gcttttagcc acttcagatg cttcgttaga atgtctccga     300
ggtctgcaac atagaaagaa gagacttcat ttgttatttg gtgttcagaa tgtccttagc     360
agtaaagcct tcctcaagga tacagcagta aaactcctcc ttagtaaagc tgctcaatgt     420
tcttcatgtg cctacagaaa acctagagat ggaattaaat tatcgccagc tccttacaag     480
gccaccttat ccaagaactg tgaatacaga ctccttgaaa tgttggaaac actcacagca     540
caggggctcg gctggctgga ccaatgggaga cactgaatcc tgaagagcac ctagctgtct     600
gctgcttcat catgtctact gaagtgaggt gtcaccaagc tgctggctaa gggaggaatg     660
tggaggtggc tgcaggaact gacctccaca attctcttac tgccccactc attatgcctt     720
```

```
ctcttctcca tcttcttctt tctttcctct ccctcctct ttcccttttca cttctttttt      780
cctttcttct tttccacttc ccttttcttt tgctgttgct gttggaaagg atttattctt      840
tcctcgtgat tgaaccaacg gatgttttac tattatttct gtaaaactca tctgttgatt      900
ttttattaat tggttaatta atcaattttg tttacactcc atattttatt caaccctcc      960
atcctcctac tgctctacat accataccc ctacccacac cccagtctcc tcatggatac     1020
tgctagctcc catgccacgt gacctctaat ctccctaggg catctggact cttgaggctt     1080
aggtgcttca cttctgaatg aacacagatc cagcagtcct ctgctgtatg tgtgttggtg     1140
gcctcatatc agctggtgta tgctgcctgt ttggtgatcc agtgtttaag agatctctgg     1200
ggtccagaat aattgagact gttgtatctc ctcagtgtct ttcagtcttt ccctgattca     1260
acattagggg tcattgtttc tgtccattgg tggctacaaa tatctgcatg tgactcagct     1320
gcttgtggg aatgcagtca tgctaggtcc cttttctatga gtgctccata gcctcagtga     1380
tagtgtcagg ccttgtggct gccacttgag ctggattcca ctttgggcct atcactggat     1440
cttcttttct tcaggctccc ctccatttcc atccctgtaa ttctttcagc caggaacaaa     1500
tatgggtcag agttgttagt gtggaatggc accctcttcc ctcatttgat ccctgtctt      1560
cctgatggag gtgggctcta aagttcact ctccctactg ttgggcattt catcccttg       1620
attcccgaga gtctctcacc tcccaggtct ctggtgcatt ctggagggtc ctcccaacct     1680
cctacctccc gaggttacct gttgacagtc tttctgctgg ccctcagtgt tcagtccttt     1740
ttctctcacc caatatctga ttttgatgga agcctgtcat gagaacatct atagacttgt     1800
ggtttcagag cttttaaattg gtctttgagc ttcaattttg acttccttcc cagtgattac     1860
ttcctgtctt tggtagtatt tttgactgtc tatttaaccc ggatactctc aaacagctgt     1920
gtaatttact tccttatttg atgactgctt tgcatagatc cctagagcca gcacagctgc     1980
ccatgattta taaaccaggt cttttgcagtg agatctgaaa tacatcagac cagcatgggc     2040
atcaagatgg agacacattc tcaggtcttt gtatacatgt tgctgtggtt gtctggtgag     2100
acatttaaaaa gtattataaa atcttaaaag taatttattt aaatagctat ttcctatagg     2160
aagccaatat taggcagaca atgccattag ataagacatt ttggattcta acatttgtat     2220
catgaagtct tatatgtgta agtgtataca cattatctgt ttctgtttgc aggtgtcgac     2280
ggagatatcg aaagtaatta atactatggt caccatccaa gagattggat cggagaataa     2340
gcatgagtag ttattgagat ctgggtctga ctgcaggtag cgtggtcttc tagacgttta     2400
agtgggagat ttggagggga tgaggaatga aggaacttca ggatagaaaa gggctgaagt     2460
caagttcagc tcctaaaatg gatgtgggag caaactttga agataaactg aatgacccag     2520
aggatgaaac agcgcagatc aaagagggc ctagagctct gagaagagaa ggagactcat      2580
ccgtgttgag tttccacaag tactgtcttg agttttgcaa taaaagtggg atagcagagt     2640
tgagtgtnag ccgtanagta tactctcttt tgtctcctaa gatttttatg actacaaaaa     2700
tcagtagtat gtcctgaaat aatcattaag ctgtttgaaa gtatgactgc ttgccatgta     2760
gataccatgg cttgctgaat gatcagaaga ggtgtgactc ttattctaaa atttgtcaca     2820
aaatgtcaaa atgagagact ctgtaggaac gagtcccttg acagacagct gcaaggggtt     2880
ttttcctttt gtctcatttc tacatgaaag taaatttgaa atgatcnttt tttattataa     2940
gagtagaaat acagttgggt ttgaactata tgttttaatn ggccncacgg ttttgtaaga     3000
catttggtcc tttgttttcc cagttattac tcgattgtaa ttttatatcg ccagcantgg     3060
tctgaaacgg tnnnnnncgc aacctcttcg tttactaact gggtgacctt cggctgtgcc     3120
```

```
agccatttgg cgttcaccct gccgcnggcc natgagaacc cccgcggtag nnccettgct   3180 ccgcgggaac cactttcctg aggacacagt gataggaaca gagccactaa tctgaagaga   3240
acagagatgt gacagactac actaatgtga gaaaacaag gaaagggtga cttattggag    3300
atttcagaaa taaatgcat ttattattat attcccttat ttaatttcta ttgggaatta    3360
gaaagggcat aaactgcttt atccagtgtt atattaaaag cttcgtaccc aattcgccct   3420
atagtgagtc gtattacgcg cgctcactgg ccgtcgtttt acaacgtcgt gactgggaaa   3480
accctggcgt tacccaactt aatcgccttg cagcacatcc cctttcgcc agctggcgta    3540 atagcgaaga ggcccgcacc gatcgccctt cccaacagtt gcgcagcctg aatggcgaat   3600
gggacgcgcc ctgtagcggc gcattaagcg cggcgggtgt ggtggttacg cgcagcgtga   3660
ccgctacact tgccagcgcc ctagcgcccg ctcctttcgc tttcttccct tcctttctcg   3720
ccacgttcgc cggctttccc cgtcaagctc taaatcgggg gctcccttta gggttccgat   3780
ttagtgcttt acggcacctc gacccaaaa acttgattta gggtgatggt tcacgtagtg    3840
ggccatcgcc ctgatagacg gttttttcgcc ctttgacgtt ggagtccacg ttctttaata  3900
gtggactctt gttccaaact ggaacaacac tcaaccctat ctcggtctat tcttttgatt   3960
tataagggat tttgccgatt tcggcctatt ggttaaaaaa tgagctgatt taacaaaaat   4020
ttaacgcgaa ttttaacaaa atattaacgc ttacaattta ggtggcactt tcggggaaa    4080 tgtgcgcgga acccctattt gtttattttt ctaaatacat tcaaatatgt atccgctcat   4140
gagacaataa cccttgataa atgcttcaat aatattgaaa aaggaagagt atgagtattc   4200
aacatttccg tgtcgccctt attccctttt ttgcggcatt ttgccttcct gttttgctc    4260 acccagaaac gctggtgaaa gtaaaagatg ctgaagatca gttgggtgca cgagtgggtt   4320
acatcgaact ggatctcaac agcggtaaga tccttgagag ttttcgcccc gaagaacgtt   4380
ttccaatgat gagcactttt gatcagaaaa aaggatcat atcgtcaatt attacctcca    4440
cggggagagc ctgagcaaac tggcctcagg catttgagaa gcacacggtc acactgcttc   4500
cggtagtcaa taaaccggta aaccagcaat agacataagc ggctatttaa cgaccctgcc   4560
ctgaaccgac gaccgggtcg aatttgcttt cgaatttctg ccattcatcc gcttattatc   4620
acttattcag gcgtagcaac caggcgttta agggcaccaa taactgcctt aaaaaaatta   4680
cgccccgccc tgccactcat cgcagtactg ttgtaattca ttaagcattc tgccgacatg   4740
gaagccatca caaacggcat gatgaacctg aatcgccagc ggcatcagca ccttgtcgcc   4800
ttgcgtataa tatttgccca tggtgaaaac gggggcgaag aagttgtcca tattggccac   4860
gtttaaatca aaactggtga aactcaccca gggattggct gagacgaaaa acatattctc   4920
aataaaccct ttagggaaat aggccaggtt ttcaccgtaa cacgccacat cttgcgaata   4980
tatgtgtaga aactgccgga aatcgtcgtg gtattcactc cagagcgatg aaaacgtttc   5040
agtttgctca tggaaaacgg tgtaacaagg gtgaacacta tcccatatca ccagctcacc   5100
gtctttcatt gccatacgta attccggatg agcattcatc aggcgggcaa gaatgtgaat   5160
aaaggccgga taaaacttgt gcttattttt ctttacggtc tttaaaaagg ccgtaatatc   5220
cagctgaacg gtctggttat aggtacattg agcaactgac tgaaatgcct caaaatgttc   5280
tttacgatgc cattgggata tatcaacggt ggtatatcca gtgatttttt tctccatttt   5340
agcttcctta gctcctgaaa atctcgacaa ctcaaaaaat acgcccggta gtgatcttat   5400
ttcattatgt tgaaagttgg aacctcttac gtgccgatca acgtctcatt tcgccaaaa   5460 gttggcccag ggcttcccgg tatcaacagg gacaccagga tttatttatt ctgcgaagtg   5520
```

```
atcttccgtc acaggtattt attcggtcga aaaggatcta ggtgaagatc cttttttgata      5580 atctcatgac caaaatccct taacgtgagt tttcgttcca ctgagcgtca gaccccgtag      5640
aaaagatcaa aggatcttct tgagatcctt ttttttctgcg cgtaatctgc tgcttgcaaa     5700
caaaaaaacc accgctacca gcggtggttt gtttgccgga tcaagagcta ccaactcttt     5760
ttccgaaggt aactggcttc agcagagcgc agataccaaa tactgtcctt ctagtgtagc     5820
cgtagttagg ccaccacttc aagaactctg tagcaccgcc tacatacctc gctctgctaa     5880
tcctgttacc agtggctgct gccagtggcg ataagtcgtg tcttaccggg ttggactcaa     5940
gacgatagtt accggataag gcgcagcggt cgggctgaac ggggggttcg tgcacacagc     6000
ccagcttgga gcgaacgacc tacaccgaac tgagatacct acagcgtgag ctatgagaaa     6060
gcgccacgct tcccgaaggg agaaaggcgg acaggtatcc ggtaagcggc agggtcggaa    6120
caggagagcg cacgagggag cttccagggg gaaacgcctg gtatctttat agtcctgtcg    6180
ggtttcgcca cctctgactt gagcgtcgat ttttgtgatg ctcgtcaggg gggcggagcc    6240
tatggaaaaa cgccagcaac gcggccttt tacggttcct ggccttttgc tggccttttg     6300
ctcacatgtt ctttcctgcg ttatccctg attctgtgga taaccgtatt accgcctttg     6360
agtgagctga taccgctcgc cgcagccgaa cgaccgagcg cagcgagtca gtgagcgagg    6420
aagcggaaga gcgcccaata cgcaaaccgc ctctccccgc gcgttggccg attcattaat    6480
gcagctggca cgacaggttt cccgactgga aagcgggcag tgagcgcaac gcaattaatg    6540
tgagttagct cactcattag gcaccccagg ctttacactt tatgcttccg gctcgtatgt    6600
tgtgtggaat tgtgagcgga taacaatttc acacaggaaa cagctatgac catgattacg    6660
ccaagcgcgc aattaaccct cactaaaggg aacaaaagct g                        6701
```

<210> SEQ ID NO 4  
<211> LENGTH: 9734  
<212> TYPE: DNA  
<213> ORGANISM: Artificial Sequence  
<220> FEATURE:  
<223> OTHER INFORMATION: Vector suitable for mammalian cells  
<220> FEATURE:  
<221> NAME/KEY: unsure  
<222> LOCATION: (3258)  
<223> OTHER INFORMATION: Wherein n can be a, c, t or g

<400> SEQUENCE: 4

```
ctcgagaccg aagctttttt tttttcagtc tatttaatta tttcaatatc tctcatcaaa       60
tgtatttaaa taacaaaagc tcaaccaaaa agaaagaaat atgtaattct ttcagagtaa      120
aaatcacacc catgacctgg ccactgaggg cttatcaatt cactttgaat ttggcattaa      180
ataccattaa ggtatattaa ctgattttaa aataagatat gtccgtgacc atgtttttaa      240 cttttcaaaaa tgtagctgcc agtgtgtgat tttatttcag ttgtacaaaa tatctaaacc      300
tatagcaatg tgattaataa aaacttaaac atattttccg agtaccttaa ttctgtgata      360
ggaaaatttt taatctgagt attttaattt cataatctct aaaatagttt aatgatttgt      420
cattgtgttg ctgtcgttta ccccagctga tctcaaaagt gatatttaag gagattattt      480
tggtctgcaa caacttgata ggactatttt agggcctttt taaagctcta ttaaaactaa      540
cttacaacga ttcaaaactg ttttaaaact atttcaaaat gattttagag ccttttgaaa      600
actcttttaa aacactttttt aaactctatt aaaactaata agataacttg aaataatttt      660
catgtcaaat acattaactg tttaatgtaa atgccagatg aaaaagtaaa gctatcaaga      720
attcacccag ataggagtat cttcatagca tgttttttccc tgcttatttt ccagtgatca      780
```

```
cattattttg ctaccatggt tattttatac aattatctga aaaaaattag ttatgaagat    840
taaaagagaa gaaatatta aacataagag attcagtctt tcatgttgaa ctgcttggtt    900
aacagtgaag ttagttttaa aaaaaaaaaa aaactatttc tgttatcagc tgacttctcc    960
ctatctgttg acttctccca gcaaaagatt cttattttac attttaacta ctgctctccc   1020
acccaacggg tggaatcccc cagaggggga tttccaagag gccacctggc agttgctgag   1080
ggtcagaagt gaagctagcc acttcctctt aggcaggtgg ccaagattac agttgacctc   1140
tcctggtatg gctgaaaatt gctgcatatg gttacagcct tgaggccttt gggagggctt   1200
agagagttgc tggaacagtc agaaggtgga ggggctgaca ccacccaggc gcagaggcag   1260
ggctcagggc ctctgctgca gggaggtttt agcccagccc agccaaagta accccggga    1320 gcctgttatc ccagcacagt cctggaagag gcacagggga aataaaagcg gacggaggct   1380
ttccttgact cagccgctgc ctggtcttct tcagacctgt tctgaattct aaactctgag   1440
ggggtcggat gacgtggcca ttcttgcct aaagcattga gtttactgca aggtcagaaa    1500
agcatgcaaa gccctcagaa tggctgcaaa gagctccaac aaaacaattt agaactttat   1560
taaggaatag ggggaagcta ggaagaaact caaaacatca agattttaaa tacgcttctt   1620
ggtctccttg ctataattat ctgggataag catgctgttt tctgtctgtc cctaacatgc   1680
cctgtgatta tccgcaaaca acacacccaa gggcagaact tgttacttaa acaccatcc    1740 tgtttgcttc tttcctcagg aactgtggct gcaccatctg tcttcatctt cccgccatct   1800
gatgagcagt tgaaatctgg aactgcctct gttgtgtgcc tgctgaataa cttctatccc   1860
agagaggcca agtacagtg gaaggtggat aacgccctcc aatcgggtaa ctcccaggag   1920
agtgtcacag gcaggacag caaggacagc acctacagcc tcagcagcac cctgacgctg   1980
agcaaagcag actacgagaa acacaaagtc tacgcctgcg aagtcaccca tcagggcctg   2040
agctcgcccg tcacaaagag cttcaacagg ggagagtgtt agagggagaa gtgccccac   2100 ctgctcctca gttccagcct gacccctcc catccttggg cctctgaccc ttttccaca    2160 ggggacctac ccctattgcg gtcctccagc tcatcttca cctcacccc ctcctcctcc    2220 ttggctttaa ttatgctaat gttggaggag aatgaataaa taaagtgaat ctttgcacct   2280
gtggtttctc tctttcctca atttaataat tattatctgt tgtttaccaa ctactcaatt   2340
tctcttataa gggactaaat atgtagtcat cctaaggcgc ataaccattt ataaaaatca   2400
tccttcattc tattttaccc tatcatcctc tgcaagacag tcctccctca aacccacaag   2460
ccttctgtcc tcacagtccc ctgggccgtg gtaggagaga cttgcttcct tgttttcccc   2520
tcctcagcaa gccctcatag tccttttaa gggtgacagg tcttacggtc atatatcctt    2580
tgattcaatt ccctgggaat caaccaaggc aaattttca aaagaagaaa cctgctataa   2640
agagaatcat tcattgcaac atgatataaa ataacaacac aataaaagca attaaataaa   2700
caaacaatag ggaaatgttt aagttcatca tggtacttag acttaatgga atgtcatgcc   2760
ttatttacat ttttaaacag gtactgaggg actcctgtct gccaagggcc gtattgagta   2820 cttttccacaa cctaatttaa tccacactat actgtgagat taaaaacatt cattaaaatg   2880
ttgcaaaggt tctataaagc tgagagacaa atatattcta taactcagca atcccacttc   2940
tagatgactg agtgtcccca cccaccaaaa aactatgcaa gaatgttcaa agcagcttta   3000
tttacaaaag ccaaaaattg gaaatagccc gattgtccaa caatagaatg agttattaaa   3060
ctgtggtatg tttatacatt agaatcccca atgaggagaa ttaacaagct acaactatac   3120
ctactcacac agatgaatct cataaaaata atgttacata agagaaactc aatgcaaaag   3180
```

```
atatgttctg tatgttttca tccatataaa gttcaaaacc aggtaaaaat aaagttagaa    3240
atttggatgg aaattacnct tagctggggg tgggcgagtt agtgcctggg agaagacaag    3300
aagggcttc  tggggtcttg gtaatgttct gttcctcgtg tggggttgtg cagttatgat    3360
ctgtgcactg ttctgtatac acattatgct tcaaaataac ttcacataaa gaacatctta    3420
tacacagtta atagatagaa gaggaataag taataggtca agaccacgca gctggtaagt    3480
ggggggggcct gggatcaaat agctacctgc ctaatcctgc cctcttgagc cctgaatgag   3540
tctgccttcc agggctcaag gtgctcaaca aaacaacagg cctgctattt tcctggcatc    3600
tgtgccctgt ttggctagct aggagcacac atacatagaa attaaatgaa acagaccttc    3660
agcaagggga cagaggacag aattaaccbt gcccagagac tggaaaccca tgtatgaaca    3720
ctcacatgtt tgggaagggg aagggcaca  tgtaaatgag gctcttcctc attctatggc    3780
actctgccct gccctctca  gctactcatc catccaacac accttctaa  gtacctctct    3840
ctgcctacac tctgaagggg ttcaggagta actaacacag catcccttcc ctcaaatgac    3900
tgacaatccc tttgtcctgc tttgtttttc tttccagtca gtactgggaa agtgggaagg    3960
acagtcatgg agaaactaca taaggaagca ccttgccctt ctgcctcttg agaatgttga    4020
tgagtatcaa atctttcaaa ctttggaggt ttgagtaggg gtgagactca gtaatgtccc    4080
ttccaatgac atgaacttgc tcactcatcc ctggggcca  aattgaacaa tcaaaggcag    4140
gcataatcca gttatgaatt ccaaaccttc ttctcagaag ataacactct gaagtgaaac    4200
ccacccataa cctaagcaag tgaagacagg tgctgcaggt ggaattgtgt ccttcaaaaa    4260
ggtatgctca actccttgct cttggtactc ataaatgggt cacataaatg tgactttatt    4320
tggaaatagg gtctttgcag aggtaatcaa gtcaaaatta ggtcatactg aaatgtttgt    4380
gaggatgcgg tgaaaatgga tcattcatat attgctggtg ggaatataaa agggtatagc    4440
tactctagaa aatagttgtc agtttcttga aaaactaaac aaaagacacc taccatatga    4500
cccaggaatt gtactccttg ggaatttacc cccaggaaat aaaaaattat gtccatatag    4560
aacccataca tgattgttca cagcagcttt atttgttgta gccaaagcta gaaagagcca    4620
acccatccct caataggcaa ctagcctaac aaattgtaat atatccatgc catagaatgc    4680
tatgaggcaa taaaaggaa  cgaagtgttg atacagagaa ctggagtgat tctgaaggac    4740
tttctactga gtgaaaaaag ccaatctgaa agggtcacat accatgtgat tcctttatg    4800
taacattgtt gaagtgacaa aattataggg atagagaaca gattctggtt gccaggggtt    4860
agggtggtgg agaaagaaga gtaggcgaaa ctataaaggg agatctttgt gatcatggga    4920
taaatctgta tcttgattgc agtggtagtt gcaggcatct agacatgtga taaaatgaca    4980
tagaactgta cacacttatt ttatcaatgt caaattcttg gttttaatat cgtactgtaa    5040
ttacgtaaga agtaaccaac aggagaaact gggtgcagga cacatcagac ctctgtgctt    5100
tatatcctgt ctttgctact ttctgtgaat ctataattat ttccaaataa tttttttaaa    5160
cttttttttt atgctggatc cggtcgaccg gatccagaca tgataagata cattgatgag    5220
tttggacaaa ccacaactag aatgcagtga aaaaatgct  ttatttgtga aatttgtgat    5280
gctattgctt tatttgtaac cattataagc tgcaataaac aagttaacaa caacaattgc    5340
attcatttta tgtttcaggt tcaggggag  gtgtgggagg ttttttaaag caagtaaaac    5400
ctctacaaat gtggtatggc tgattatgat ctctagtcaa ggcactatac atcaaatatt    5460
ccttattaac ccctttacaa attaaaaagc taaaggtaca caattttga  gcatagttat    5520
taatagcaga cactctatgc ctgtgtggag taagaaaaaa cagtatgtta tgattataac    5580
```

```
tgttatgcct acttataaag gttacagaat attttttccat aatttttcttg tatagcagtg    5640 cagcttttc  ctttgtggtg taaatagcaa agcaagcaag agttctatta ctaaacacag    5700
catgactcaa aaaacttagc aattctgaag gaaagtcctt ggggtcttct acctttctct    5760
tcttttttgg aggagtagaa tgttgagagt cagcagtagc ctcatcatca ctagatggca    5820
tttcttctga gcaaaacagg ttttcctcat taaaggcatt ccaccactgc tcccattcat    5880
cagttccata ggttggaatc taaaatacac aaacaattag aatcagtagt ttaacacatt    5940
atacacttaa aaatttttata tttaccttag agctttaaat ctctgtaggt agtttgtcca    6000
attatgtcac accacagaag taaggttcct tcacaaagat ccggggccca ctcataaatc    6060
cagttgccgc cacggtagcc aatcaccgta tcgtataaat catcgtcggt acgttcggca    6120
tcgctcatca caatacgtgc ctggacgtcg aggatttcgc gtgggtcaat gccgcgccag    6180
atccacatca gacggttaat catgcgatac cagtgaggga tggttttacc atcaagggcc    6240
gactgcacag gcggttgtgc gccgtgatta aagcggcgga ctagcgtcga ggtttcagga    6300
tgtttaaagc ggggtttgaa cagggtttcg ctcaggtttg cctgtgtcat ggatgcagcc    6360
tccagaatac ttactggaaa ctattgtaac ccgcctgaag ttaaaaagaa caacgcccgg    6420
cagtgccagg cgttgaaaag attagcgacc ggagattggc gggacgaata cgacgcccat    6480
atcccacggc tgttcaatcc aggtatcttg cgggatatca acaacatagt catcaaccag    6540
cggacgacca gccggttttg cgaagatggt gacaaagtgc gcttttggat acatttcacg    6600
aatcgcaacc gcagtaccac cggtatccac caggtcatca ataacgatga agccttcgcc    6660
atcgccttct gcgcgtttca gcactttaag ctcgcgctgg ttgtcgtgat cgtagctgga    6720
aatacaaacg gtatcgacat gacgaatacc cagttcacgc gccagtaacg cacccggtac    6780
cagaccgcca cggcttacgg caataatgcc tttccattgt tcagaaggca tcagtcggct    6840
tgcgagttta cgtgcatgga tctgcaacat gtcccaggtg acgatgtatt tttcgctcat    6900
gtgaagtgtc ccagcctgtt tatctacggc ttaaaaagtg ttcgagggga aaataggttg    6960
cgcgagatta tagagatctg gcgcactaaa aaccagtatt tcacatgagt ccgcgtctttt   7020 ttacgcactg cctctccctg acgcgggata aagtggtatt ctcaaacata tctcgcaagc    7080
ctgtcttgtg tccaagctag cttttttgcaa aagcctaggc ctccaaaaaa gcctcctcac    7140
tacttctgga atagctcaga ggccgaggcg gcctcggcct ctgcataaat aaaaaaaatt    7200
agtcagccat ggggcggaga atgggcggaa ctgggcggag ttaggggcgg gatgggcgga    7260
gttaggggcg ggactatggt tgctgactaa ttgagatgca tgctttgcat acttctgcct    7320
gctggggagc ctggttgctg actaattgag atgcatgctt tgcatacttc tgcctgctgg    7380
ggagcctggg gactttccac accctaactg acacacattc cacagctgcc tcgcgcgttt    7440
cggtgatgac ggtgaaaacc tctgacacat gcagctcccg gagacggtca cagcttgtct    7500
gtaagcggat gccgggagca gacaagcccg tcagggcgcg tcagcgggtg ttggcgggtg    7560
tcggggcgca gccatgaccc agtcacgtag cgatagcgga gtgtatactg gcttaactat    7620
gcggcatcag agcagattgt actgagagtg caccatatgc ggtgtgaaat accgcacaga    7680
tgcgtaagga gaaaataccg catcaggcgc tcttccgctt cctcgctcac tgactcgctg    7740
cgctcggtcg ttcggctgcg gcgagcggta tcagctcact caaaggcggt aatacggtta    7800
tccacagaat caggggataa cgcaggaaag aacatgtgag caaaaggcca gcaaaaggcc    7860
aggaaccgta aaaaggccgc gttgctggcg ttttccata  ggctccgccc ccctgacgag    7920
catcacaaaa atcgacgctc aagtcagagg tggcgaaacc cgacaggact ataaagatac    7980
```

| | |
|---|---|
| caggcgtttc ccctggaag ctccctcgtg cgctctcctg ttccgaccct gccgcttacc | 8040 |
| ggatacctgt ccgcctttct cccttcggga agcgtggcgc tttctcatag ctcacgctgt | 8100 |
| aggtatctca gttcggtgta ggtcgttcgc tccaagctgg gctgtgtgca cgaaccccc | 8160 |
| gttcagcccg accgctgcgc cttatccggt aactatcgtc ttgagtccaa cccggtaaga | 8220 |
| cacgacttat cgccactggc agcagccact ggtaacagga ttagcagagc gaggtatgta | 8280 |
| ggcggtgcta cagagttctt gaagtggtgg cctaactacg gctacactag aaggacagta | 8340 |
| tttggtatct gcgctctgct gaagccagtt accttcggaa aaagagttgg tagctcttga | 8400 |
| tccggcaaac aaaccaccgc tggtagcggt ggttttttg tttgcaagca gcagattacg | 8460 |
| cgcagaaaaa aaggatctca agaagatcct ttgatctttt ctacggggtc tgacgctcag | 8520 |
| tggaacgaaa actcacgtta agggattttg gtcatgagat tatcaaaaag gatcttcacc | 8580 |
| tagatccttt taaattaaaa atgaagtttt aaatcaatct aaagtatata tgagtaaact | 8640 |
| tggtctgaca gttaccaatg cttaatcagt gaggcaccta tctcagcgat ctgtctattt | 8700 |
| cgttcatcca tagttgcctg actccccgtc gtgtagataa ctacgatacg ggagggctta | 8760 |
| ccatctggcc ccagtgctgc aatgataccg cgagacccac gctcaccggc tccagattta | 8820 |
| tcagcaataa accagccagc cggaagggcc gagcgcagaa gtggtcctgc aactttatcc | 8880 |
| gcctccatcc agtctattaa ttgttgccgg gaagctagag taagtagttc gccagttaat | 8940 |
| agtttgcgca acgttgttgc cattgctgca ggcatcgtgg tgtcacgctc gtcgtttggt | 9000 |
| atggcttcat tcagctccgg ttcccaacga tcaaggcgag ttacatgatc ccccatgttg | 9060 |
| tgcaaaaaag cggttagctc cttcggtcct ccgatcgttg tcagaagtaa gttggccgca | 9120 |
| gtgttatcac tcatggttat ggcagcactg cataattctc ttactgtcat gccatccgta | 9180 |
| agatgctttt ctgtgactgg tgagtactca accaagtcat tctgagaata gtgtatgcgg | 9240 |
| cgaccgagtt gctcttgccc ggcgtcaaca cgggataata ccgcgccaca tagcagaact | 9300 |
| ttaaaagtgc tcatcattgg aaaacgttct cggggcgaa aactctcaag gatcttaccg | 9360 |
| ctgttgagat ccagttcgat gtaacccact cgtgcaccca actgatcttc agcatctttt | 9420 |
| actttcacca gcgtttctgg gtgagcaaaa acaggaaggc aaaatgccgc aaaaaaggga | 9480 |
| ataagggcga cacggaaatg ttgaatactc atactcttcc tttttcaata ttattgaagc | 9540 |
| atttatcagg gttattgtct catgagcgga tacatatttg aatgtattta gaaaaataaa | 9600 |
| caaatagggg ttccgcgcac atttccccga aaagtgccac ctgacgtcta agaaaccatt | 9660 |
| attatcatga cattaaccta taaaaatagg cgtatcacga ggccctttcg tcttcaagaa | 9720 |
| gaattccagc tatg | 9734 |

<210> SEQ ID NO 5
<211> LENGTH: 5173
<212> TYPE: DNA
<213> ORGANISM: Artificial Sequence
<220> FEATURE:
<223> OTHER INFORMATION: Vector suitable for mammalian cells
<220> FEATURE:
<221> NAME/KEY: J_segment
<222> LOCATION: (1304)
<223> OTHER INFORMATION: Wherein n can be a, c, t or g

<400> SEQUENCE: 5

| | |
|---|---|
| tctagagaag actttagagt agaatctgag gctcacctca cataccagca agggagtgac | 60 |
| cagttagtct taaggcacca ctgagcccaa gtcttagaca tcatggcttg ggtgtggacc | 120 |
| ttgctattcc tgatggcagc tgcccaaagt aagacatcag aaaaaaagag ttccaaggga | 180 |

```
aattgaagca gttccatgaa tactcacctt cctgtgttct tttcacaggt atacaggcct    240
ctgtcccctg ctccactcct taaagagacc aggaagtttc tcccccaacg caagacagac    300
acaagcagac agaatctcag agaaaagagg tttattgggt ttcacagatg gtgcaggggg    360
tccctgtgga tgtctagcca agcagtggct ggcttttaga gcttcgtgct ttcttctaga    420
accccttggt cacccacatc taattctctc gccatctctc tcttagatgg gtcctgtctg    480
aggtgagaca cctttgtgtc tgggacctag ttgtcatctg acggctttct attttccc    540 tctttctatt ctctataaat aaataactta acttttctct ccataaatag tcaaccttcc    600
cctgttccca gccacctctc ccatgtctgt ccctccttca tgtccaggtc tctgtccgac    660
ctagacccac aaaaacctg ctctgtgcag gaacttctag gtaggcttga gtcgtccct    720 gagcatctgg agtggccctg gggaagatgt agtcccctga agtgtctcag actcccgtga    780
gagctccagg ttattttagt ggggaaggct ggagactgtg gggatgtgac ccttgaaaca    840
acggtcagga tggaggcctg gaatccaatt cttgggtttc tttagaatct acagtgcaaa    900
ggctccaaag aatacactgc tgggctgaa gtgtagatgg gagatgccgt cggtgtgggt    960
ggacagctgg tctcccttac tgagcaggaa cacagccccc tggtacattg agcgcaccca   1020
cggtccttga agtcccggat acacagactt ctgcgcactg aggagaggca catggaaggg   1080
gtattgggag gaaaagagct ggacctcgtg tgccaggtag atgggagtgg gaatggccct   1140
gggggagcag ctttctccag agaaaaccac ctgggagtag acaaagtaga ggccactggt   1200
ggggatcagg agggagttgt tgctcaaaga gaagccatgt cggagaaagg cacgatccgt   1260
gcttgctctc cagagcagtg agttctgctt gctggggtac cacngtcacc gtctcctcag   1320
gtaagaatgg cctctccagg tctttatttt taaccttgt tatggagttt tctgagcatt   1380
gcagactaat cttggatatt tgccctgagg gagccggctg agagaagttg ggaaataaat   1440
ctgtctaggg atctcagagc ctttaggaca gattatctcc acatctttga aaaactaaga   1500
atctgtgtga tggtgttggt ggagtccctg atgatggga tagggacttt ggaggctcat   1560
ttgagggaga tgctaaaaca atcctatggc tggagggata gttggggctg tagttggaga   1620
ttttcagttt ttagaatgaa gtattagctg caatacttca aggaccacct ctgtgacaac   1680
cattttatac agtatccagg catagggaca aaaagtggag tggggcactt tctttagatt   1740
tgtgaggaat gttccacact agattgttta aaacttcatt tgttggaagg agctgtctta   1800
gtgattgagt caagggagaa aggcatctag cctcggtctc aaaagggtag ttgctgtcta   1860
gaggatctga gctccagctt tgttcccctt tagtgttaat tgcgcgcttg gcgtaatcat   1920
ggtcatagct gtttcctgtg tgaaattgtt atccgctcac aattccacac aacatacgag   1980
ccggaagcat aaagtgtaaa gcctggggtg cctaatgagt gagctaactc acattaattg   2040
cgttgcgctc actgcccgct ttccagtcgg gaaacctgtc gtgccagctg cattaatgaa   2100
tcggccaacg cgcgggaga gcggtttgc gtattgggcg ctcttccgct tcctcgctca   2160
ctgactcgct gcgctcggtc gttcggctgc ggcgagcggt atcagctcac tcaaaggcgg   2220
taatacggtt atccacagaa tcaggggata acgcaggaaa gaacatgtga gcaaaaggcc   2280
agcaaaaggc caggaaccgt aaaaaggccg cgttgctggc gtttttccat aggctccgcc   2340
cccctgacga gcatcacaaa aatcgacgct caagtcagag gtggcgaaac ccgacaggac   2400
tataaagata ccaggcgttt ccccctggaa gctccctcgt gcgctctcct gttccgaccc   2460
tgccgcttac cggatacctg tccgcctttc tcccttcggg aagcgtggcg ctttctcata   2520
gctcacgctg taggtatctc agttcggtgt aggtcgttcg ctccaagctg ggctgtgtgc   2580
```

```
acgaaccccc cgttcagccc gaccgctgcg ccttatccgg taactatcgt cttgagtcca    2640
acccggtaag acacgactta tcgccactgg cagcagccac tggtaacagg attagcagag    2700
cgaggtatgt aggcggtgct acagagttct tgaagtggtg gcctaactac ggctacacta    2760
gaaggacagt atttggtatc tgcgctctgc tgaagccagt taccttcgga aaaagagttg    2820
gtagctcttg atccggcaaa caaaccaccg ctggtagcgg tggttttttt gtttgcaagc    2880
agcagattac gcgcagaaaa aaggatctc aagaagatcc tttgatcttt tctacggggt    2940
ctgacgctca gtggaacgaa aactcacgtt aagggatttt ggtcatgaga ttatcaaaaa    3000
ggatcttcac ctagatcctt ttcgaccgaa taaatacctg tgacggaaga tcacttcgca    3060
gaataaataa atcctggtgt ccctgttgat accgggaagc cctgggccaa cttttgcga    3120 aaatgagacg ttgatcggca cgtaagaggt tccaactttc accataatga ataagatca    3180 ctaccgggcg tatttttga gttgtcgaga ttttcaggag ctaaggaagc taaaatggag    3240
aaaaaaatca ctggatatac caccgttgat atatcccaat ggcatcgtaa agaacatttt    3300
gaggcatttc agtcagttgc tcaatgtacc tataaccaga ccgttcagct ggatattacg    3360 gccttttaa agaccgtaaa gaaaaataag cacaagtttt atccggcctt tattcacatt    3420
cttgcccgcc tgatgaatgc tcatccggaa ttacgtatgg caatgaaaga cggtgagctg    3480
gtgatatggg atagtgttca cccttgttac accgttttcc atgagcaaac tgaaacgttt    3540
tcatcgctct ggagtgaata ccacgacgat ttccggcagt ttctacacat atattcgcaa    3600
gatgtggcgt gttacggtga aaacctggcc tatttcccta aagggtttat tgagaatatg    3660
tttttcgtct cagccaatcc ctgggtgagt ttcaccagtt ttgatttaaa cgtggccaat    3720
atggacaact tcttcgcccc gttttcacca tgggcaaata ttatacgcaa ggcgacaagg    3780
tgctgatgcc gctggcgatt caggttcatc atgccgtttg tgatggcttc catgtcggca    3840
gaatgcttaa tgaattacaa cagtactgcg atgagtggca gggcggggcg taattttttt    3900
aaggcagtta ttggtgccct aaacgcctg gttgctacgc ctgaataagt gataataagc    3960
ggatgaatgg cagaaattcg aaagcaaatt cgacccggtc gtcggttcag ggcagggtcg    4020
ttaaatagcc gcttatgtct attgctggtt taccggttta ttgactaccg gaagcagtgt    4080
gaccgtgtgc ttctcaaatg cctgaggcca gtttgctcag gctctccccg tggaggtaat    4140
aattgacgat atgatccttt ttttctgatc aaaagtgctc atcattggaa aacgttcttc    4200
ggggcgaaaa ctctcaagga tcttaccgct gttgagatcc agttcgatgt aacccactcg    4260
tgcacccaac tgatcttcag catctttac tttcaccagc gtttctgggt gagcaaaaac    4320
aggaaggcaa aatgccgcaa aaagggaat aagggcgaca cggaaatgtt gaatactcat    4380
actcttcctt tttcaatatt attgaagcat ttatcaaggg ttattgtctc atgagcggat    4440
acatatttga atgtatttag aaaaataaac aaataggggt tccgcgcaca tttccccgaa    4500
aagtgccacc taaattgtaa gcgttaatat tttgttaaaa ttcgcgttaa attttgtta    4560 aatcagctca ttttttaacc aataggccga atcggcaaa atcccttata atcaaaaga    4620 atagaccgag atagggttga gtgttgttcc agtttggaac aagagtccac tattaaagaa    4680
cgtggactcc aacgtcaaag ggcgaaaaac cgtctatcag ggcgatggcc cactacgtga    4740
accatcaccc taatcaagtt ttttggggtc gaggtgccgt aaagcactaa atcggaaccc    4800
taaagggagc ccccgattta gagcttgacg gggaaagccg gcgaacgtgg cgagaaagga    4860
agggaagaaa gcgaaaggag cgggcgctag ggcgctggca agtgtagcgg tcacgctgcg    4920
cgtaaccacc acacccgccg cgcttaatgc gccgctacag ggcgcgtccc attcgccatt    4980
```

```
caggctgcgc aactgttggg aagggcgatc ggtgcgggcc tcttcgctat tacgccagct    5040
ggcgaaaggg ggatgtgctg caaggcgatt aagttgggta acgccagggt tttcccagtc    5100
acgacgttgt aaaacgacgg ccagtgagcg cgcgtaatac gactcactat agggcgaatt    5160
gggtacactc gac                                                       5173

<210> SEQ ID NO 6
<211> LENGTH: 5173
<212> TYPE: DNA
<213> ORGANISM: Artificial Sequence
<220> FEATURE:
<223> OTHER INFORMATION: Vector suitable for mammalian cells

<400> SEQUENCE: 6
tctagagaag actttagagt agaatctgag gctcacctca cataccagca agggagtgac      60
cagttagtct taaggcacca ctgagcccaa gtcttagaca tcatggcttg ggtgtggacc     120
ttgctattcc tgatggcagc tgcccaaagt aagacatcag aaaaaaagag ttccaaggga     180
aattgaagca gttccatgaa tactcacctt cctgtgttct tttcacaggt atacaggcct     240
ctgtcccctg ctccactcct taaagagacc aggaagtttc tccccaacg caagacagac      300 acaagcagac agaatctcag agaaaagagg tttattgggt ttcacagatg gtgcaggggg    360
tccctgtgga tgtctagcca agcagtggct ggcttttaga gcttcgtgct ttcttctaga    420 acccccttggt cacccacatc taattctctc gccatctctc tcttagatgg gtcctgtctg   480
aggtgagaca cctttgtgtc tgggacctag ttgtcatctg acggctttct attttttccc    540
tctttctatt ctctataaat aaataactta acttttctct ccataaatag tcaaccttcc    600
cctgttccca gccacctctc ccatgtcgt ccctccttca tgtccaggtc tctgtccgac     660
ctagacccac aaaaaccctg ctctgtgcag gaacttctag gtaggcttga gtcgtcccct    720
gagcatctgg agtggccctg gggaagatgt agtcccctga agtgtctcag actcccgtga    780
gagctccagg ttattttagt ggggaaggct ggagactgtg gggatgtgac ccttgaaaca    840
acggtcagga tggaggcctg gaatccaatt cttgggtttc tttagaatct acagtgcaaa    900
ggctccaaag aatacactgc tggggctgaa gtgtagatgg gagatgccgt cggtgtgggt    960
ggacagctgg tctcccttac tgagcaggaa cacagccccc tggtacattg agcgcaccca   1020
cggtccttga agtcccggat acacagactt ctgcgcactg aggagaggca catggaaggg   1080
gtattgggag gaaaagagct ggacctcgtg tgccaggtag atgggagtgg gaatggccct   1140
gggggagcag ctttctccag agaaaaccac ctggagtag acaaagtaga ggccactggt    1200
ggggatcagg agggagttgt tgctcaaaga gaagccatgt cggagaaagg cacgatccgt   1260
gcttgctctc cagagcagtg agttctgctt gctggggtac catggtcacc gtctcctcag   1320
gtaagaatgg cctctccagg tctttatttt taacctttgt tatggagttt tctgagcatt   1380
gcagactaat cttggatatt tgccctgagg gagccggctg agagaagttg ggaaataaat   1440
ctgtctaggg atctcagagc ctttaggaca gattatctcc acatctttga aaaactaaga   1500
atctgtgtga tggtgttggt ggagtccctg gatgatggga tagggacttt ggaggctcat   1560
ttgagggaga tgctaaaaca atcctatggc tggagggata gttggggctg tagttggaga   1620
ttttcagttt ttagaatgaa gtattagctg caatacttca aggaccacct ctgtgacaac   1680
cattttatac agtatccagg catagggaca aaaagtggag tggggcactt tctttagatt   1740
tgtgaggaat gttccacact agattgttta aaacttcatt tgttggaagg agctgtctta   1800
gtgattgagt caagggagaa aggcatctag cctcggtctc aaaagggtag ttgctgtcta   1860
```

```
gaggatctga gctccagctt ttgttccctt tagtgttaat tgcgcgcttg cgtaatcat    1920
ggtcatagct gtttcctgtg tgaaattgtt atccgctcac aattccacac aacatacgag    1980
ccggaagcat aaagtgtaaa gcctggggtg cctaatgagt gagctaactc acattaattg    2040
cgttgcgctc actgcccgct ttccagtcgg gaaacctgtc gtgccagctg cattaatgaa    2100
tcggccaacg cgcggggaga ggcggtttgc gtattgggcg ctcttccgct tcctcgctca    2160
ctgactcgct gcgctcggtc gttcggctgc ggcgagcggt atcagctcac tcaaaggcgg    2220
taatacggtt atccacagaa tcaggggata cgcaggaaa gaacatgtga gcaaaaggcc    2280
agcaaaaggc caggaaccgt aaaaaggccg cgttgctggc gttttttccat aggctccgcc    2340
cccctgacga gcatcacaaa aatcgacgct caagtcagag gtggcgaaac ccgacaggac    2400
tataaagata ccaggcgttt ccccctggaa gctccctcgt gcgctctcct gttccgaccc    2460
tgccgcttac cggatacctg tccgcctttc tcccttcggg aagcgtggcg ctttctcata    2520
gctcacgctg taggtatctc agttcggtgt aggtcgttcg ctccaagctg gctgtgtgc    2580
acgaaccccc cgttcagccc gaccgctgcg ccttatccgg taactatcgt cttgagtcca    2640
acccggtaag acacgactta tcgccactgg cagcagccac tggtaacagg attagcagag    2700
cgaggtatgt aggcggtgct acagagttct tgaagtggtg cctaactac ggctacacta    2760
gaaggacagt atttggtatc tgcgctctgc tgaagccagt taccttcgga aaagagttg    2820
gtagctcttg atccggcaaa caaaccaccg ctggtagcgg tggtttttttt gtttgcaagc    2880
agcagattac gcgcagaaaa aaggatctc aagaagatcc tttgatcttt tctacggggt    2940
ctgacgctca gtggaacgaa aactcacgtt aagggatttt ggtcatgaga ttatcaaaaa    3000
ggatcttcac ctagatcctt ttcgaccgaa taaatacctg tgacggaaga tcacttcgca    3060
gaataaataa atcctggtgt ccctgttgat accgggaagc cctgggccaa cttttggcga    3120
aaatgagacg ttgatcggca cgtaagaggt tccaactttc accataatga aataagatca    3180
ctaccgggcg tattttttga gttgtcgaga ttttcaggag ctaaggaagc taaaatggag    3240
aaaaaaatca ctggatatac caccgttgat atatcccaat ggcatcgtaa agaacatttt    3300
gaggcatttc agtcagttgc tcaatgtacc tataaccaga ccgttcagct ggatattacg    3360
gcctttttaa agaccgtaaa gaaaaataag cacaagtttt atccggcctt tattcacatt    3420
cttgcccgcc tgatgaatgc tcatccggaa ttacgtatgg caatgaaaga cggtgagctg    3480
gtgatatggg atagtgttca cccttgttac accgttttcc atgagcaaac tgaaacgttt    3540
tcatcgctct ggagtgaata ccacgacgat ttccggcagt ttctacacat atattcgcaa    3600
gatgtggcgt gttacggtga aaacctggcc tatttcccta aagggtttat tgagaatatg    3660
ttttttcgtct cagccaatcc ctgggtgagt ttcaccagtt ttgatttaaa cgtggccaat    3720
atggacaact tcttcgcccc gttttcacca tgggcaaata ttatacgcaa ggcgacaagg    3780
tgctgatgcc gctggcgatt caggttcatc atgccgtttg tgatggcttc catgtcggca    3840
gaatgcttaa tgaattacaa cagtactgcg atgagtggca gggcggggcg taatttttt    3900
aaggcagtta ttggtgccct aaacgcctg gttgctacgc ctgaataagt gataataagc    3960
ggatgaatgg cagaaattcg aaagcaaatt cgacccggtc gtcggttcag gcagggtcg    4020
ttaaatagcc gcttatgtct attgctggtt taccggttta ttgactaccg gaagcagtgt    4080
gaccgtgtgc ttctcaaatg cctgaggcca gtttgctcag gctctccccg tggaggtaat    4140
aattgacgat atgatccttt ttttctgatc aaaagtgctc atcattggaa aacgttcttc    4200
ggggcgaaaa ctctcaagga tcttaccgct gttgagatcc agttcgatgt aacccactcg    4260
```

-continued

```
tgcacccaac tgatcttcag catcttttac tttcaccagc gtttctgggt gagcaaaaac    4320
aggaaggcaa aatgccgcaa aaaagggaat aagggcgaca cggaaatgtt gaatactcat    4380
actcttcctt tttcaatatt attgaagcat ttatcaaggg ttattgtctc atgagcggat    4440
acatatttga atgtatttag aaaaataaac aaatagggt tccgcgcaca tttccccgaa     4500
aagtgccacc taaattgtaa gcgttaatat tttgttaaaa ttcgcgttaa atttttgtta    4560
aatcagctca tttttaacc aataggccga aatcggcaaa atcccttata aatcaaaaga     4620
atagaccgag ataggttga gtgttgttcc agtttggaac aagagtccac tattaaagaa     4680
cgtggactcc aacgtcaaag ggcgaaaaac cgtctatcag ggcgatggcc cactacgtga    4740
accatcaccc taatcaagtt ttttggggtc gaggtgccgt aaagcactaa atcggaaccc    4800 taagggagc ccccgattta gagcttgacg gggaaagccg gcgaacgtgg cgagaaagga     4860
agggaagaaa gcgaaaggag cgggcgctag ggcgctggca agtgtagcgg tcacgctgcg    4920
cgtaaccacc acaccccgccg cgcttaatgc gccgctacag ggcgcgtccc attcgccatt   4980
caggctgcgc aactgttggg aagggcgatc ggtgcgggcc tcttcgctat tacgccagct    5040
ggcgaaaggg ggatgtgctg caaggcgatt aagttggta acgccagggt ttcccagtc      5100 acgacgttgt aaaacgacgg ccagtgagcg cgcgtaatac gactcactat agggcgaatt    5160
gggtacactc gac                                                       5173
```

<210> SEQ ID NO 7
<211> LENGTH: 29
<212> TYPE: PRT
<213> ORGANISM: Artificial Sequence
<220> FEATURE:
<223> OTHER INFORMATION: CD4 Based Vector

<400> SEQUENCE: 7

```
Met Gly Ile Lys Met Glu Thr His Ser Gln Val Phe Val Tyr Met Leu
 1               5                  10                  15

Leu Trp Leu Ser Gly Glu Thr Phe Lys Ser Val Asp Gly
            20                  25
```

<210> SEQ ID NO 8
<211> LENGTH: 29
<212> TYPE: PRT
<213> ORGANISM: Artificial Sequence
<220> FEATURE:
<223> OTHER INFORMATION: CD4 Based Vector

<400> SEQUENCE: 8

```
Met Gly Ile Lys Met Glu Thr His Ser Gln Val Phe Val Tyr Met Leu
 1               5                  10                  15

Leu Trp Leu Ser Gly Glu Thr Phe Lys Ser Val Asp Gly
            20                  25
```